US012758626B2

(12) United States Patent
Kalergis Parra et al.

(10) Patent No.: US 12,758,626 B2
(45) Date of Patent: Oct. 13, 2026

(54) IMMUNOGENIC FORMULATION CONTAINING ONE OR MORE MODIFIED BCG STRAINS EXPRESSING A SARS-CoV-2 PROTEIN, USEFUL FOR PREVENTING, TREATING, OR ATTENUATING THE DEVELOPMENT OF COVID-19

(71) Applicants: PONTIFICIA UNIVERSIDAD CATOLICA DE CHILE, Santiago (CL); FUNDACION COPEC UNIVERSIDAD CATÓLICA, Santiago (CL)

(72) Inventors: Alexis Kalergis Parra, Santiago (CL); Susan Bueno Ramírez, Santiago (CL); Pablo Gonzalez Muñoz, Santiago (CL); Angello Retamal Diaz, Santiago (CL); Jorge Soto Ramirez, Santiago (CL)

(73) Assignees: PONTIFICIA UNIVERSIDAD CATOLICA DE CHILE, Santiago (CL); FUNDACION COPEC UNIVERSIDAD CATÓLICA, Santiago (CL)

( * ) Notice: Subject to any disclaimer, the term of this patent is extended or adjusted under 35 U.S.C. 154(b) by 546 days.

(21) Appl. No.: 18/258,943

(22) PCT Filed: Dec. 23, 2021

(86) PCT No.: PCT/CL2021/050123

§ 371 (c)(1),
(2) Date: Jun. 22, 2023

(87) PCT Pub. No.: WO2022/133622

PCT Pub. Date: Jun. 30, 2022

(65) Prior Publication Data

US 2024/0042012 A1 Feb. 8, 2024

(30) Foreign Application Priority Data

Dec. 23, 2020 (CL) .................................. 3370-2020
Dec. 14, 2021 (CL) .................................. 3346-2021

(51) Int. Cl.
*A61K 39/215* (2006.01)
*A61P 31/14* (2006.01)
*C07K 14/165* (2006.01)
*A61K 39/00* (2006.01)

(52) U.S. Cl.
CPC ............ *A61K 39/215* (2013.01); *A61P 31/14* (2018.01); *C07K 14/165* (2013.01); *A61K 2039/522* (2013.01); *A61K 2039/523* (2013.01); *A61K 2039/545* (2013.01)

(58) Field of Classification Search
None
See application file for complete search history.

(56) References Cited

U.S. PATENT DOCUMENTS

| | | | | |
|---|---|---|---|---|
| 10,010,597 | B2 * | 7/2018 | Brosch | C12N 1/20 |
| 11,253,587 | B2 * | 2/2022 | Anderson | C12N 15/86 |
| 11,713,491 | B2 * | 8/2023 | Kana | C12Q 1/6806 435/5 |
| 2021/0369836 | A1 | 12/2021 | Li | |

FOREIGN PATENT DOCUMENTS

| | | |
|---|---|---|
| CL | 2013002829 | 4/2014 |
| EP | 3 054 013 | 8/2016 |
| WO | 2021/161043 | 8/2021 |

OTHER PUBLICATIONS

De Queiroz et al. (Microbes and Infection, Sep. 2020, p. 515-524).*
Gupta, "New disease old vacine: Is recombinant BCG vaccine an answer for COVID-19?", Cellular Immunology 356 (2020) 104187, 6 pages.
N.M.G.P. de Queiroz, et al., "Vaccines for COVID-19: perspectives from nucleic acid vaccines to BCG as delivery vector system", Microbes and Infection 22 (2020) 515-524.
Khan, et al., "COVID-19 Pandemic and Vaccines Update on Challenges and Resolutions", Frontiers in Cellular and Infection Microbiology 11 (2021) 690621, 23 pages.
International Search Report issued in International Application No. PCT/CL2021/050123, Mar. 22, 2022, 16 pages w/ translation.

* cited by examiner

*Primary Examiner* — Agnieszka Boesen
(74) *Attorney, Agent, or Firm* — HSML P.C.

(57) ABSTRACT

The invention relates to an immunogenic formulation containing one or more modified recombinant strains of *Bacillus* Calmette-Guerin (BCG), in a concentration between $10^4$-$10^9$ bacteria, where each BCG strain expresses at least one protein or immunogenic fragment of SARS-CoV-2, in a pharmaceutically acceptable saline buffer, where this formulation serves to prepare vaccines to prevent, treat or attenuate SARS-CoV-2 infections.

13 Claims, 9 Drawing Sheets

Specification includes a Sequence Listing.

Resultado:
(1) rBCG-N1—SARS-CoV-2 (#2): $5,9\times10^{6}$ copies/100 ng RNA.
(2) rBCG-N2-SARS-CoV-2 (#1): $1,7\times10^{6}$ copies/100 ng RNA.
(3) rBCG-N1-SARS-CoV-2 (#1): $2,8\times10^{5}$ copies/100 ng RNA.

Resultados:
(1) rBCG-E-SARS-CoV-2 (#1): $4\times10^{3}$ copies/100 ng RNA.
(2) rBCG-E-SARS-CoV-2 (#2): $1.7\times10^{6}$ copies/100 ng RNA

IMMUNOGENIC FORMULATION CONTAINING ONE OR MORE MODIFIED BCG STRAINS EXPRESSING A SARS-CoV-2 PROTEIN, USEFUL FOR PREVENTING, TREATING, OR ATTENUATING THE DEVELOPMENT OF COVID-19

FIELD OF INVENTION

An immunogenic formulation useful for preparing a vaccine against SARS-CoV-2, the virus responsible for COVID-19, is disclosed, where this formulation comprises at least one attenuated strain of *Mycobacterium bovis, Bacillus* Calmette-Guérin (BCG), which recombinantly expresses one or more proteins or immunogenic fragments of SARS-CoV-2, useful for preventing, treating, or attenuating SARS-CoV-2 infections.

BACKGROUND OF THE INVENTION

SARS-CoV-2, is a respiratory virus discovered in December 2019 in Wuhan, Hubei province, China. It produces an acute respiratory syndrome called COVID-19 (Coronavirus disease 2019), and evidence of human-to-human transmission between close contacts was confirmed. Sequence analysis showed that this zoonotic SARS-CoV-2 virus possesses a genomic structure typical of coronaviruses and belonged to the β-coronavirus group.

The main symptoms and clinical signs of this syndrome are: fever above 38° C., dyspnea and dry cough, which can trigger pneumonia and even death in more extreme cases. Although the virus has a low average mortality rate, around 2% in the first four months of 2020, given its high degree of infectivity, it has become a major public health problem worldwide, and the World Health Organization (WHO) declared it a pandemic on Mar. 11, 2020.

Although to date COVID-19 as a declared pandemic, has spread to most countries in the world, the impact has not been the same in all countries. While this difference can be explained in part by the policies with which each country has faced the pandemic and the timing of those policies, among other factors, many researchers have correlated the lower impact of SARS-CoV-2, both on morbidity and mortality from the disease, with the policy of childhood vaccination with *Bacillus* Calmette-Guérin (BCG). It has been reported that countries without universal BCG vaccination policies (Italy, Netherlands, USA among others) have been more severely affected compared to countries with universal and long-standing BCG policies. Data indicate that BCG vaccine also reduces the number of reported cases of COVID-19 in a country (Covián, C., Retamal-Díaz, A., Bueno, S. M. and Kalergis, A. M., 2020. Could BCG vaccination induce protective trained immunity for SARS-CoV-2. Frontiers in Immunology, 11, p. 970; Miller, Aaron, et al. Correlation between universal BCG vaccination policy and reduced morbidity and mortality for COVID-19: an epidemiological study. medRxiv, 2020.).

As we know, different vaccines have been developed based on different technologies to prevent COVID-19, most of which are approved for use in adults, where some of them have emergency approval in the pediatric population, from 3 or 6 years onwards.

Although the vaccination process has slowed the progress of the pandemic, to date there is no vaccine approved for application in neonates, or in pediatric populations under 3 years of age. Additionally, it is possible that the pandemic will accompany us for many years, due to the appearance of new variants, and we must be vaccinated one or more times a year, depending on the waves or outbreaks of contagion.

Given this scenario, the inventors have developed new vaccines for COVID-19, which use as a vector the attenuated strain of *Mycobacterium bovis, Bacillus* Calmette-Guerin (BCG), which has demonstrated for more than 100 years, safe use in neonates and which is known to act as an adjuvant and induce responses that confer long-term immunity, transforming it to express a protein or immunogenic fragment of SARS-CoV-2, which allows for generation of immunity against this virus and controls the development of COVID-19, protecting the population from birth.

B. Identification of recombinant BCG strains for N-SARS-CoV-2 and S-SARS-CoV-2 genes by PCR using specific splitters. The identification of the N and S genes from the genome of the recombinant BCG strains was carried out using the specific primers for each of the genes of interest. Subsequently, the amplicon was analyzed in a 1% agarose gel, identifying amplicons of the expected size (1260 bp for N-SARS-CoV-2 and 3644 bp for S-SARS-CoV-2). "$CO_2$" means that the bacteria were grown in the presence of $CO_2$ 5%. "SC-2" is short for SARS-CoV-2.

Figure 2:
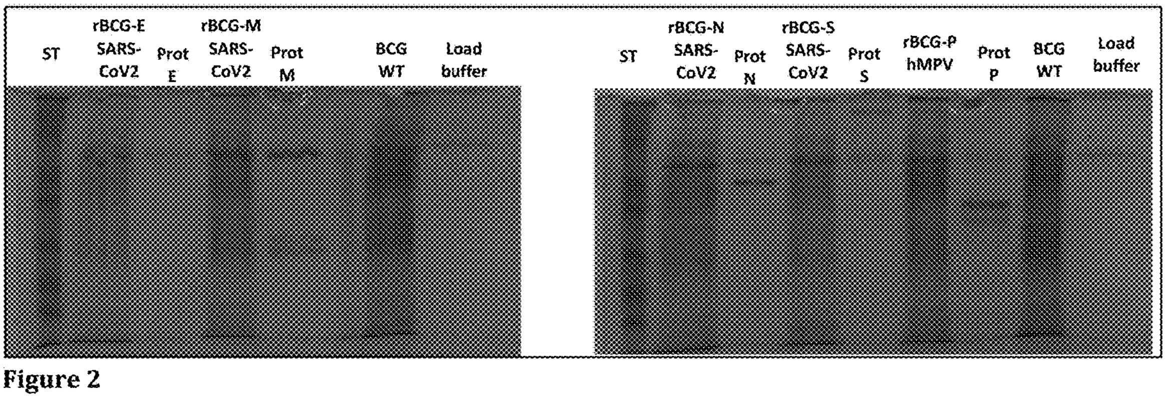

FIG. 2. Extraction of proteins from recombinant BCGs that present SARS-CoV-2 genes. The proteome of each strain is compared with the viral protein of interest, observing that in each case there is a band of similar size to the cloned protein.

FIG. 3.A Expression of the N-SARS-CoV-2 gene in recombinant BCGs. The evaluation of the copy number of the transcript for the N gene was performed from 100 ng of total RNA obtained from a culture saturated with rBCG-N-SARS-CoV-2.

B. Expression of the E-SARS-CoV2 gene from recombinant BCGs. The evaluation of the copy number of the transcript for the E gene was performed from 100 ng of total RNA obtained from a culture saturated with rBCG-E-SARS-CoV-2.

C. Expression of the M-SARS-CoV-2 gene from recombinant BCGs. The evaluation of the copy number of the transcript for the M gene was performed from 100 ng of total RNA obtained from a culture saturated with rBCG-M-SARS-CoV-2.

D. Expression of the S1/2-SARS-CoV-2 gene from recombinant BCGs. The evaluation of the copy number of the transcript for the S1/2 gene was performed from 100 ng of total RNA obtained from a culture saturated with rBCG-S1/2-SARS-CoV-2.

The numbers present in the graphs represent different RNA samples from strains that were confirmed as positive by conventional PCR. (1) RNA sample from clone 1 of the rBCG-N-SARS-CoV-2 strain in culture passage 2. (2) RNA sample from clone 2 of the rBCG-N-SARS-CoV-2 strain in culture passage 1. (3) RNA sample from clone 1 of the rBCG-N-SARS-CoV-2 strain in culture passage 1. "Neg" corresponds to the negative control that corresponds to the reaction without RNA. The number of copies was calculated by extrapolating the CT obtained for each of the samples with a standard curve previously standardized with the plasmid pUC57-N-SARS-CoV-2. The symbol (#) corresponds to the cultivation passage.

Figure 4:
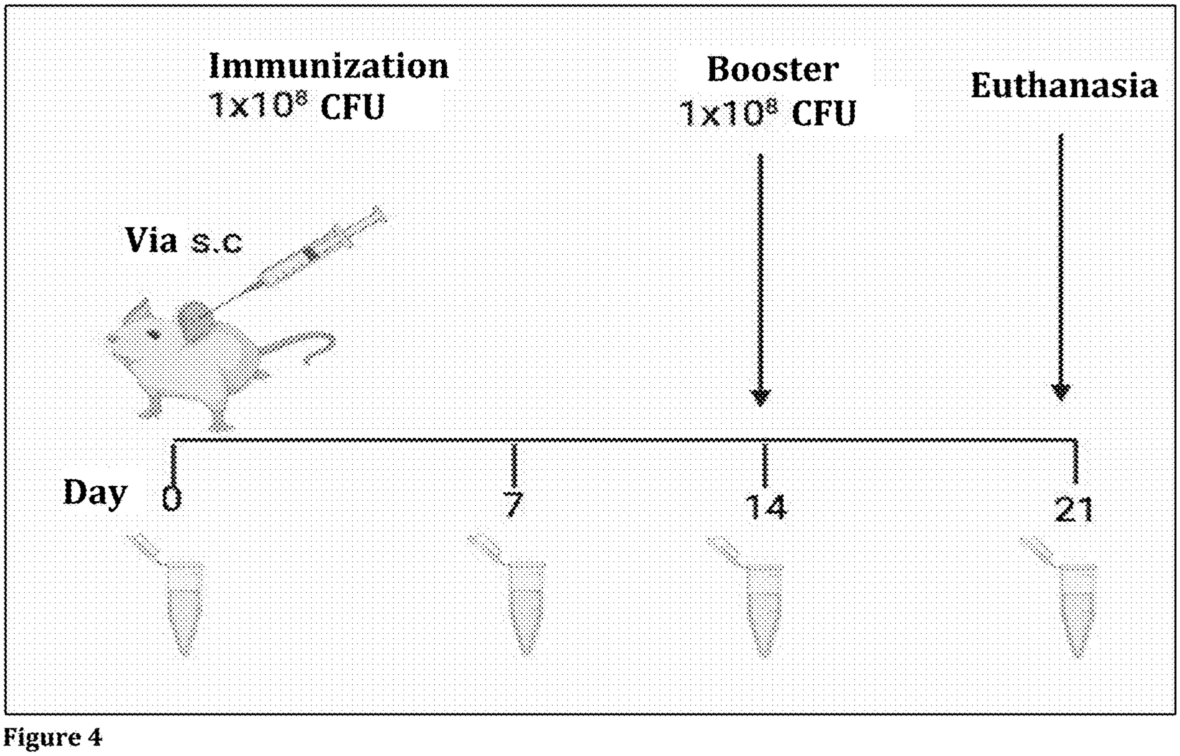

FIG. 4. Immunization schedule to evaluate the induction of anti-SARS-CoV-2 immune responses by vaccination with recombinant BCG. Days 0 and 14 correspond to the days of vaccination of animals with a dose of $1\times10^8$ CFU (Colony Forming Unit). The tubes under the days correspond to the points within the experiment at which blood samples were taken to obtain serums. Day 21 corresponds to the end point of the experiment.

Figure 5:
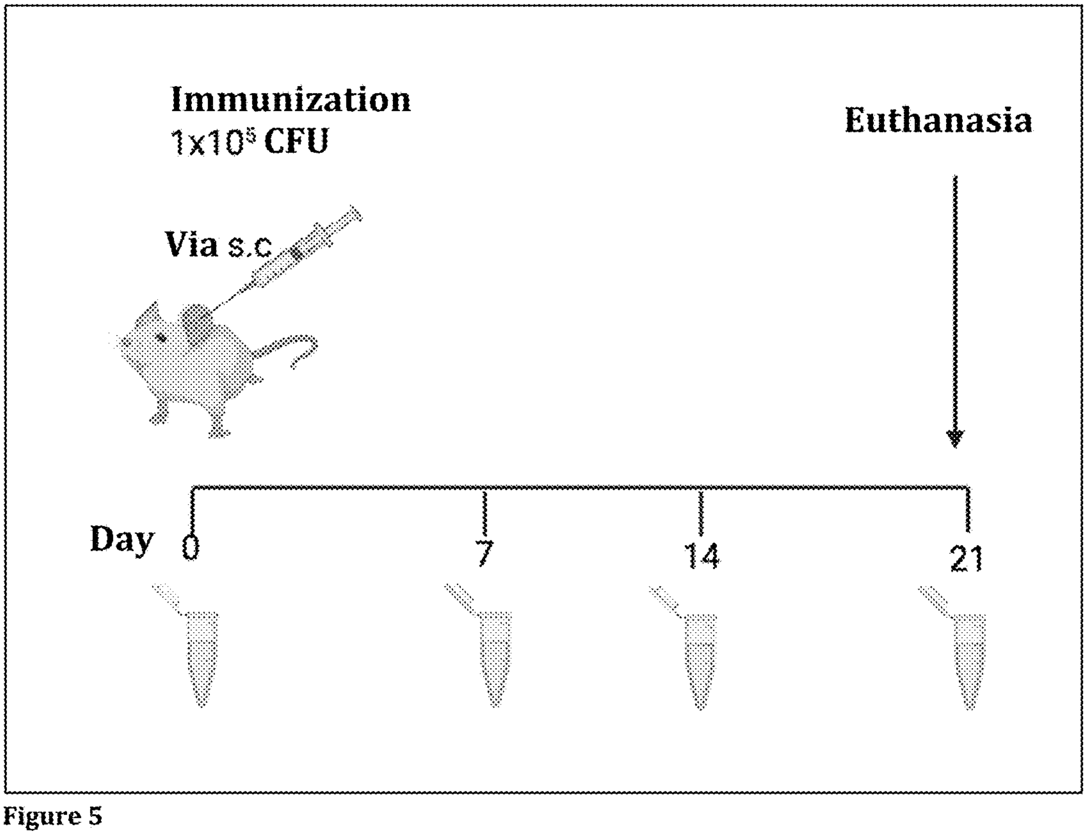

FIG. 5. Immunization schedule to evaluate the induction of anti-SARS-CoV-2 immune responses by vaccination with recombinant BCG. Day 0 corresponds to the day of vaccination of animals with a dose of $1\times10^5$ CFU. The tubes under the days correspond to the points within the experiment at which blood samples were taken to obtain serums. Day 21 corresponds to the end point of the experiment.

Figure 6:
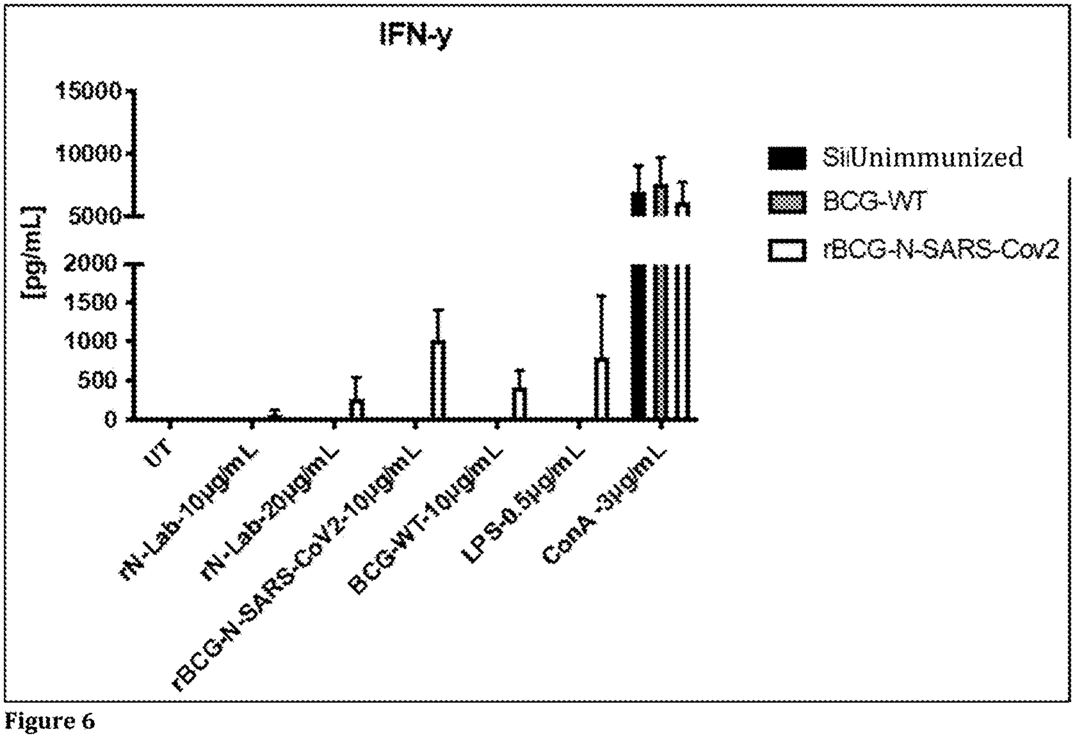

FIG. 6. Determination of cytokines resulting from vaccination with rBCG-N-SARS-CoV-2. The cytokines secreted in the co-culture consisting of dendritic cells and total T lymphocytes obtained from the spleens and lymph nodes of animals submitted to immunization schedule No 2 were evaluated. The cytokine IFN-γ was evaluated by ELISA using a dilution of the co-cultured supernatants of 1/10. The colorimetric reaction was evaluated in an ELISA reader at a wavelength of 450 nm. With A it is a stimulus that enhances the immune response, and corresponds to a positive control.

Figure 7:
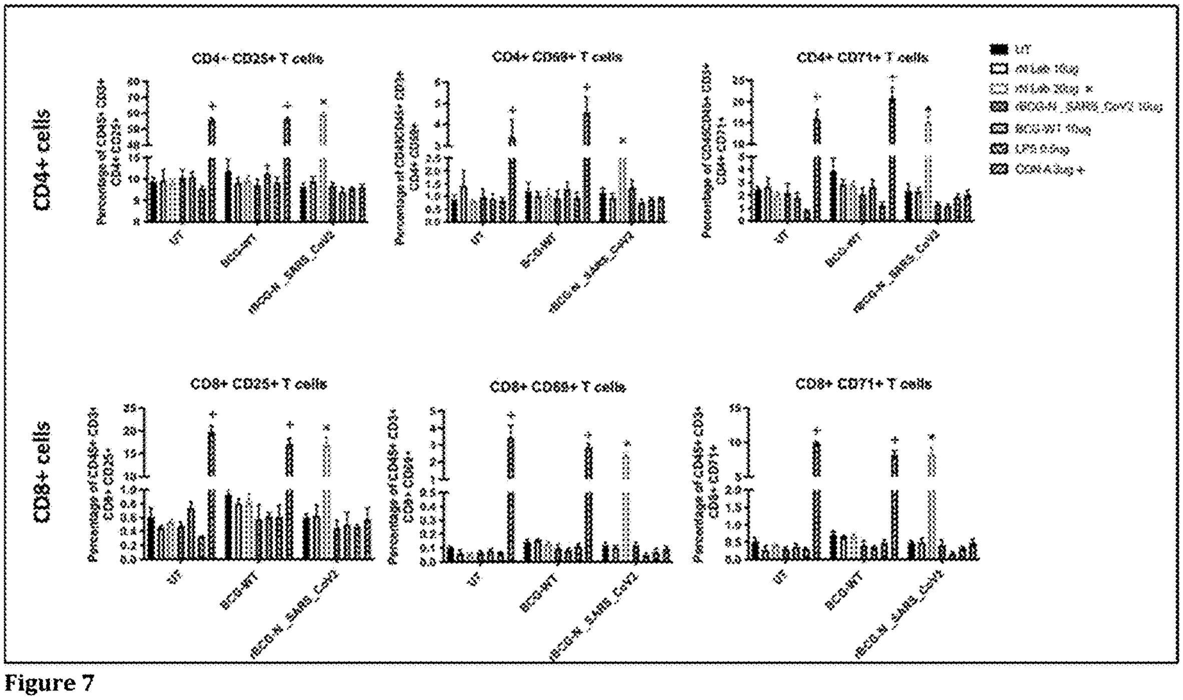

FIG. 7. Evaluation of activation markers on the surface of $CD4^+$ and $CD8^+$ T lymphocytes 72 hours post-co-culture with dendritic cells loaded with different treatments. To evaluate whether vaccination with rBCG-N-SARS-CoV-2 induces a cellular immune response, after ending the experiment, total T lymphocytes were purified from the animals' spleens. These were then co-cultured with dendritic cells loaded with different peptides and treatments for 72 hours. After this time, the activation markers $CD69^+$, $CD71^+$ and $CD25^+$ were evaluated on the surface of $CD4^+$ and $CD8^+$ T lymphocytes by flow cytometry. The upper panel, corresponds to $CD4^+$ T lymphocytes for $CD25^+$, $CD69^+$ and $CD71^+$ markers. The lower panel corresponds to $CD8^+$ T cells for the $CD25^+$, $CD69^+$, and $CD71^+$ markers. The bar marked with * corresponds to the response against SARS-CoV-2 N protein, and the bar marked with+corresponds to the control With A which is a positive control of activation of the experiment.

Figure 8:
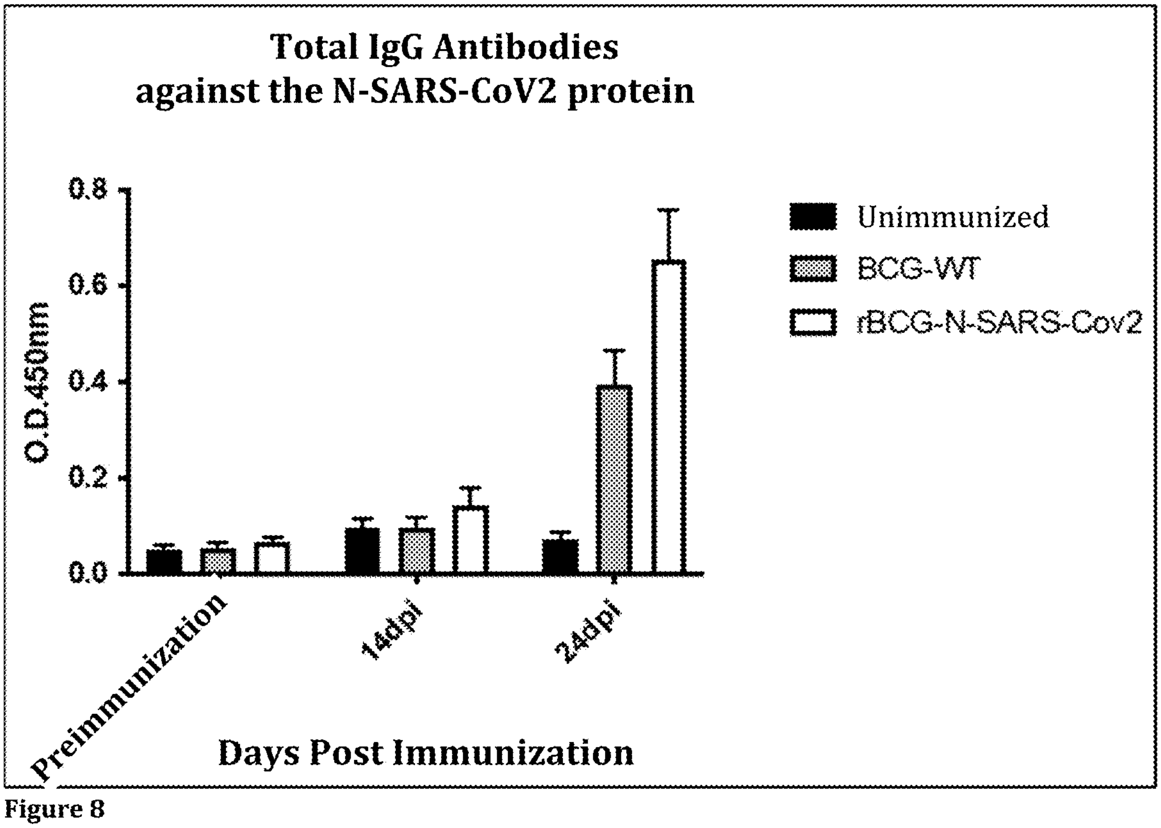

FIG. 8. Determination of SARS-CoV-2 anti-N antibodies induced by vaccination with rBCG-N-SARS-CoV-2. Antibodies secreted from sera obtained from immunized animals with two doses of $1\times10^8$ CFU were evaluated. Specific antibodies against the N protein of the virus were evaluated by ELISA using 1/600 diluted sera. The colorimetric reaction was evaluated in an ELISA reader at a wavelength of 450 nm.

Figure 9:
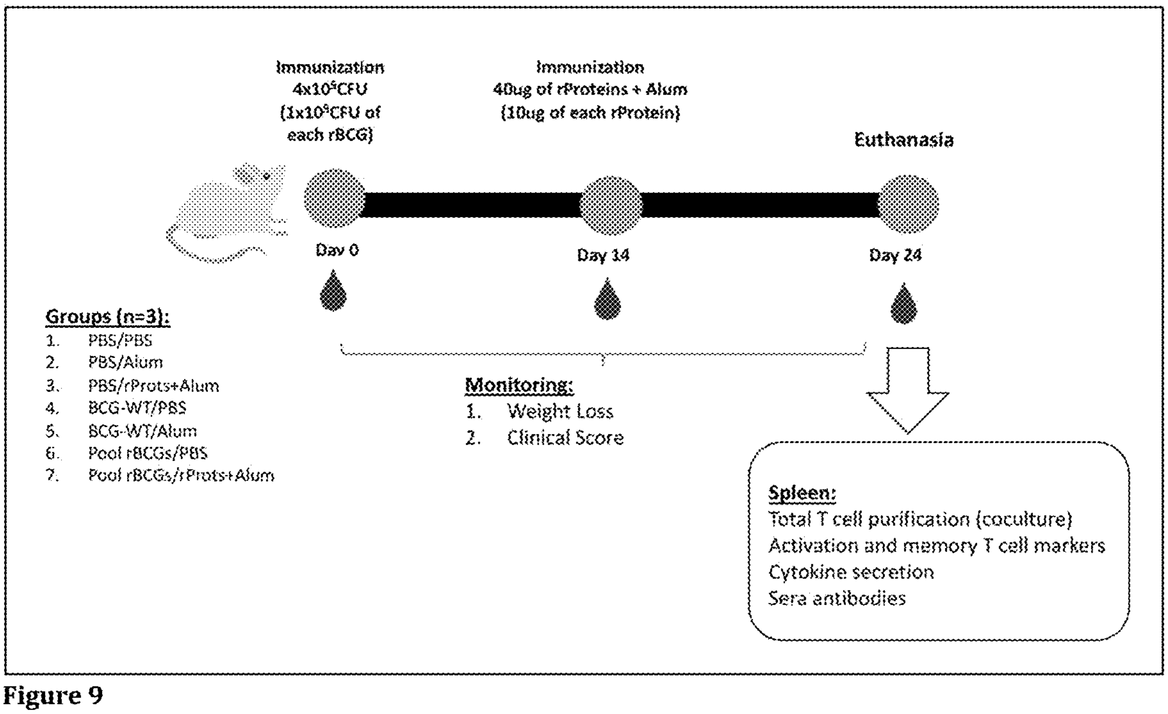

FIG. 9. Immunization schedule to evaluate the induction of anti-SARS-CoV-2 immune response by vaccination with a pool (mixture) of the recombinant BCG strains of the invention. Day 0 corresponds to the day of vaccination of animals with a dose of $4\times10^5$ CFU. Day 14 corresponds to the booster administered with purified proteins and aluminium hydroxide (Alum) or their controls respectively. The symbols under the days correspond to the points within the experiment where blood samples were taken to obtain serums. Day 24 corresponds to the end point of the experiment.

Figure 10:
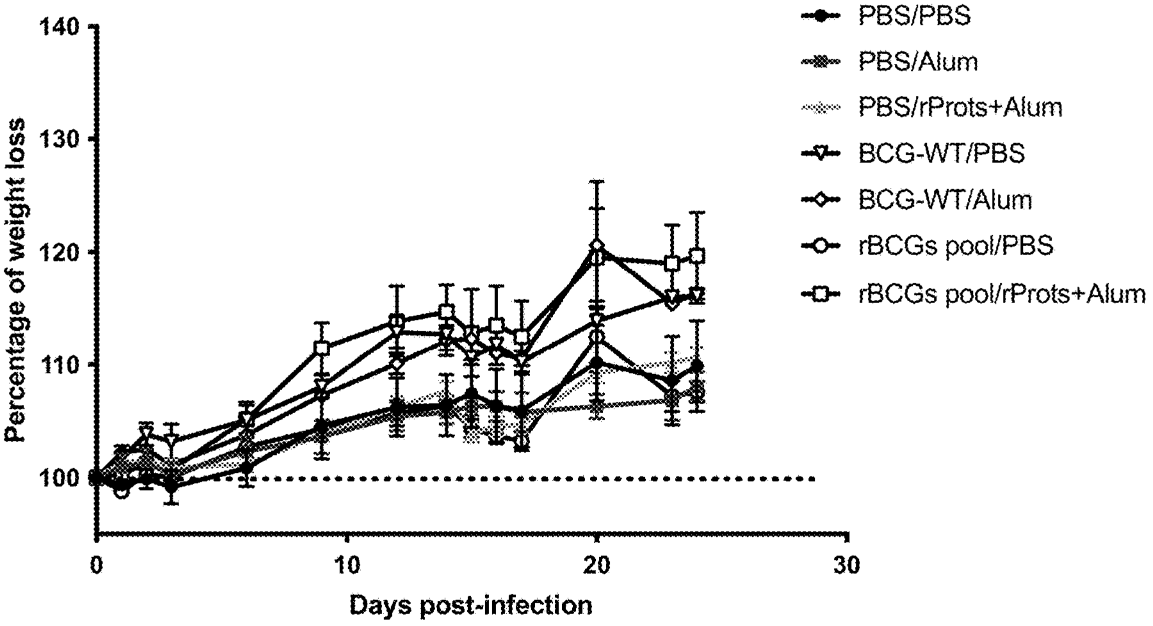

FIG. 10. Determination of the weight curve in vaccinated animals. The weight gain or loss of immunized animals was monitored with a dose of $4\times10^5$ CFU from a pool (mixture) of the recombinant strains of rBGC-N-SARS-CoV-2, rBGC-E-SARS-CoV-2, rBGC-M-SARS-CoV-2, rBGC-S-SARS-CoV-2, and their control groups for 24 days to determine if the vaccine was safe for animals.

Figure 11:
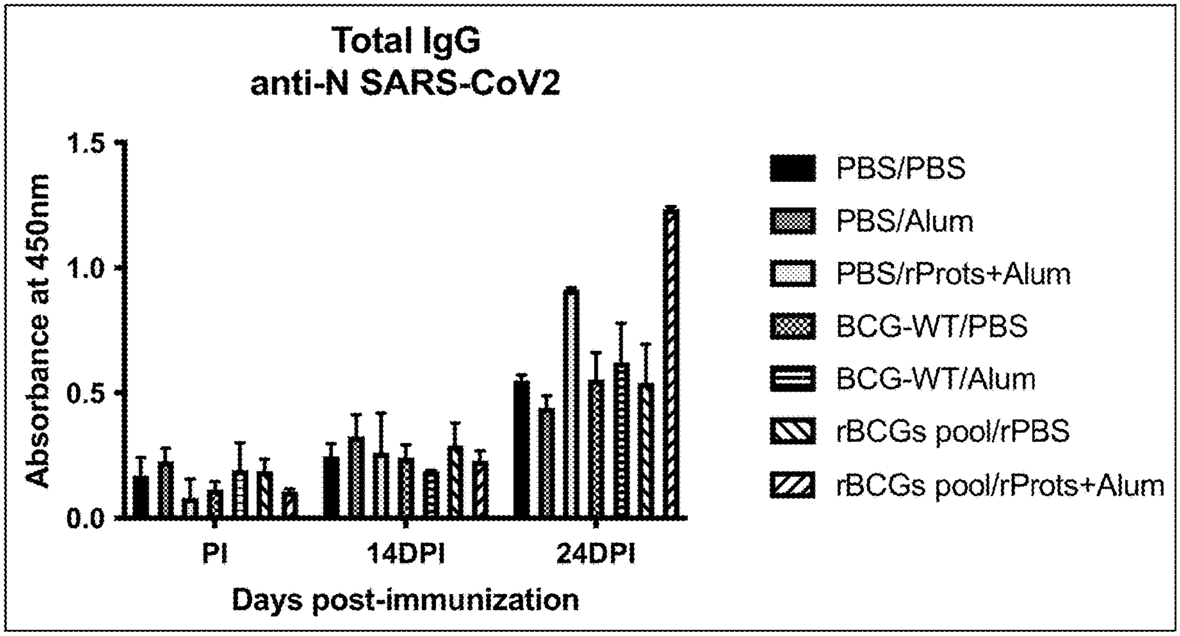

FIG. 11. Determination of SARS-CoV-2 anti-N antibodies induced by vaccination with a pool (mixture) of recombinant BCG strains at a dose of $4\times10^5$ CFU. Specific antibodies against the N protein of the virus were evaluated by ELISA using diluted sera 1/5, for all the conditions indicated in Table 1. The colorimetric reaction was evaluated in an ELISA reader at a wavelength of 450 nm.

Figure 12:
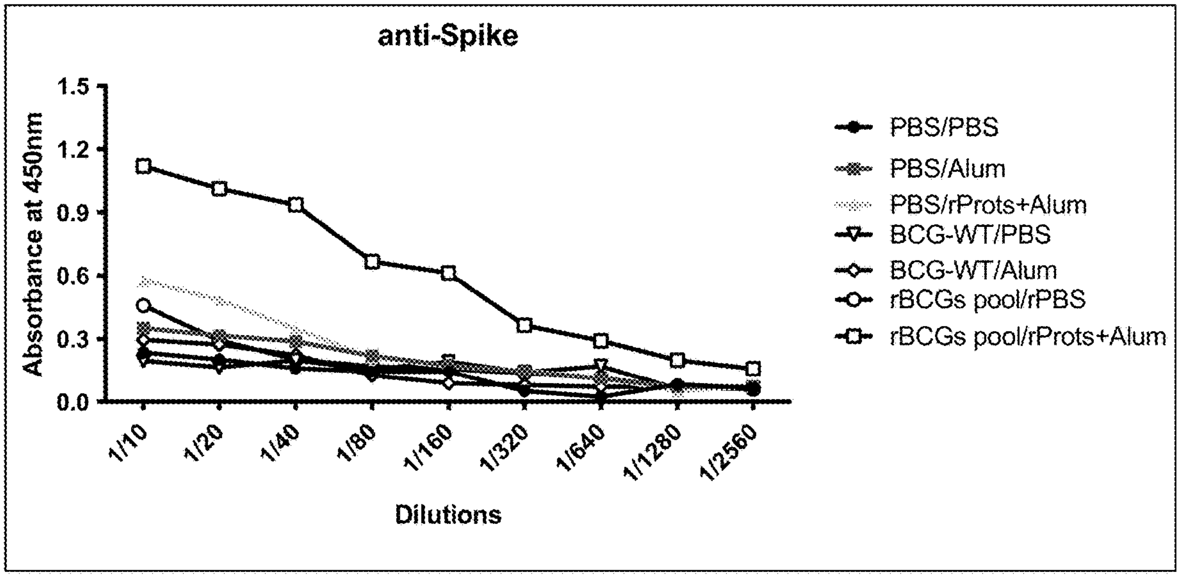

FIG. 12. Determination of SARS-CoV-2 anti-S antibodies induced by vaccination with a pool (mixture) of recombinant BCG strains at a dose of $4\times10^5$ CFU. The titer of specific antibodies against the S protein of the virus was evaluated by ELISA using sera diluted from 1/10 to 1/2560, for all the conditions indicated in Table 1. The colorimetric reaction was evaluated in an ELISA reader at a wavelength of 450 nm FIG. 13. Evaluation of activation markers on the surface of $CD8^+$ T lymphocytes at 72 hours post-co-culture with dendritic cells treated with different stimuli of proteins N, M, S, or the mixture of N, M and S, all of SARS-CoV-2. After ending the experiment, according to the scheme in Table 2, total T lymphocytes were purified from the spleens. These were then co-cultured with dendritic cells loaded with the various peptides for 72 hours. After this time, the activation markers $CD69^+$, $CD71^+$ and $CD25^+$ were evaluated on the surface of $CD8^+$ T lymphocytes by flow cytometry.

Figure 14:
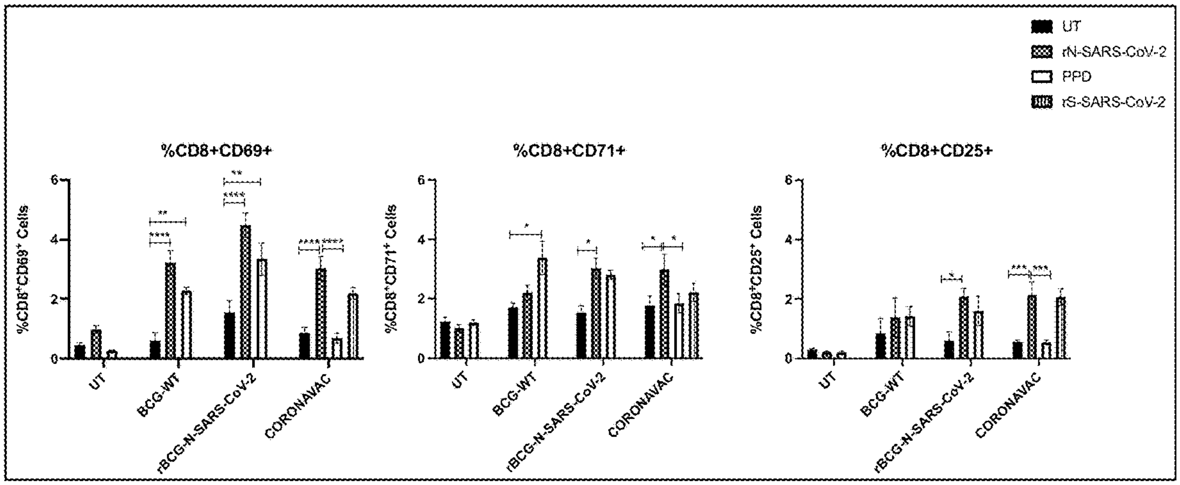

FIG. 14. Evaluation of activation markers on the surface of $CD8^+$ T lymphocytes 72 hours post-co-culture with dendritic cells treated with different stimuli, N or S proteins, or purified protein derivative (PPD). After putting an end to the experiment, and according to the scheme of Table 3, total T lymphocytes were purified from the spleens. These were co-cultured with dendritic cells loaded with different stimuli for 72 hours. After this time, the activation markers $CD69^+$, $CD71^+$ and $CD25^+$ were evaluated on the surface of $CD8^+$ T lymphocytes by flow cytometry.

Figure 15:
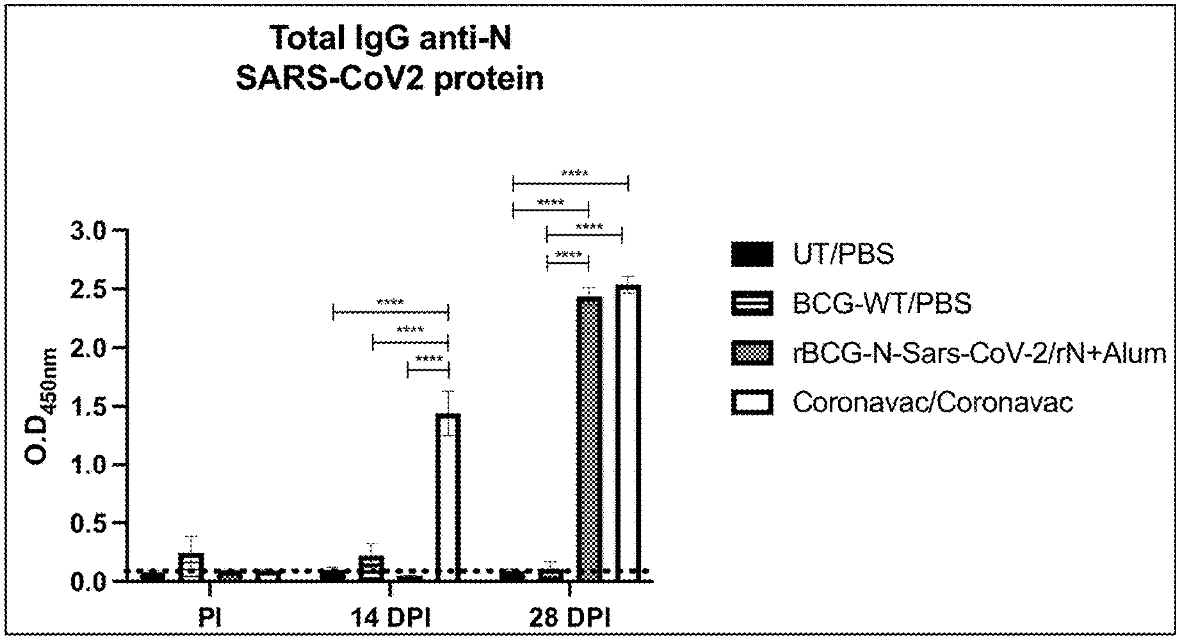

FIG. 15. Determination of SARS-CoV-2 anti-N antibodies induced by vaccination with an rBCG-N-SARS-CoV-2 strain at a dose of $1\times10^5$ CFU and a booster with recombinant N protein+Alum, and by inactivated virus vaccine. Specific antibodies against the N protein of the virus were evaluated using undiluted sera using ELISA technique. The colorimetric reaction was evaluated in an ELISA reader at a wavelength of 450 nm.

DESCRIPTION OF THE INVENTION

The invention corresponds to immunogenic formulation comprising at least one live attenuated strain based on *Mycobacterium bovis*, preferably of the *bacillus* Calmette-Guerin strain (BCG) comprising the recombinant expression of a heterologous viral antigen of SARS-CoV-2.

Coronaviruses (CoV), including SARS-CoV-2 comprise a single-stranded, positive-sense RNA ranging in size from 26,000 to 37,000 bases. This is the largest known genome among RNA viruses. The genomic structure of the CoV is as follows: tail 5'-leader-UTR-replicase-S(Spike)-E (Envelope)-M (Membrane)-N(Nucleocapsid)-3'UTRpoly (A). M and E proteins play an important role in viral assembly, and the N protein is necessary for RNA synthesis. The S Protein (Spike) is responsible for receptor binding and subsequent viral entry into host cells, Spike is a highly glycosylated trimeric class I fusion protein and contains two subunits, S1 and S2. In this document we will refer to it interchangeably as S or S1/S2.

More particularly, we can indicate that the invention corresponds to a formulation comprising at least one strain of *Bacillus* Calmette-Guerin (BCG), which expresses recombinantly (rBCG) antigens of N, E, M and/or S of the SARS-CoV-2 virus. The BCG vaccine strain has demonstrated surprising genetic stability over the years it has been in use.

The genes of interest of SARS-CoV-2 were cloned, by standard genetic engineering techniques, in the pMV361 vector of recombination and expression in *Mycobacterium*, with the resulting vector the BCG strains were transformed by electroporation. Once transformed, the level of viral antigen expression was evaluated at the protein level by Western blot and at the messenger RNA level through RT-qPCR. In addition, the genomic DNA of the transformed strains was purified to determine the integration of the genes of interest in the BCG genome.

For the person skilled in the art it will be evident that a different vector and a different transformation technique could be used than the one selected by the inventors, without this modification meaning a deterioration of the observed results, so that such modifications are considered within the scope of the present invention.

Specifically, the invention aims at an immunogenic formulation that confers protection against COVID-19, comprising at least one attenuated recombinant strain of *Mycobacterium bovis Bacillus* Calmette-Guerin (BCG), in an amount between $10^4$-$10^9$ colony forming units (CFU) per dose, which expresses at least one protein or immunogenic fragment of the SARS-CoV-2 virus, in a pharmaceutically acceptable saline buffer solution. Preferably, the protein or immunogenic fragment of SARS-CoV-2 corresponds to the N, E, M or S proteins of SARS-CoV-2 or their immunogenic fragments, where the proteins have an amino acid sequence at least 75% identical to the amino acid sequence of the products of the genes of the SEQ ID NO: 1, SEQ ID NO: 2, SEQ ID NO:3 or SEQ ID NO:4. And preferably proteins have an amino acid sequence at least 95% identical to SEQ ID NO: 1, SEQ ID NO: 2, SEQ ID NO: 3 or SEQ ID NO: 4.

The SEQ ID NO: 1 corresponds to the gene that codes for the N protein, using the restriction sites of the enzymes BstBI and ClaI. The SEQ ID NO: 2 corresponds to the gene that codes for protein E, using the restriction sites of the enzymes BstBI and ClaI. The SEQ ID NO: 3 corresponds to the gene that codes for the M protein, using the restriction sites of the enzymes BstBI and ClaI. The SEQ ID NO: 4 corresponds to the gene that codes for the S protein, using the restriction sites of the enzymes MfeI and AflII.

In the immunogenic formulation of the invention, the genes coding for the protein N, E, M or S of SARS-CoV-2 or its immunogenic fragments are inserted in the genome of *Mycobacterium* BCG or in extrachromosomal plasmids, in one or more copies, and are regulated or commanded by endogenous or exogenous promoters of *Mycobacterium* BCG, constitutive or inducible. Where the genes coding for SARS-CoV-2 protein N, E, M or S or their immunogenic fragments correspond to a nucleotide sequence at least 75% identical to SEQ ID NO:1, SEQ ID NO:2, SEQ ID NO:3 or SEQ ID NO:4., and preferably at least 95% identical to SEQ ID NO:1, SEQ ID NO:2, SEQ ID NO:3 or SEQ ID NO:4, considering all intermediate options. As a result, SARS-CoV-2 N, E, M or S proteins or their immunogenic fragments can be expressed by BCG in a soluble-cytoplasmic manner, secreted extracellularly, or as cell membrane-bound proteins. The BCG strain used is preferably chosen between BCG Danish or BCG Pasteur.

In an embodiment of the invention, the protein or immunogenic fragment of the SARS-CoV-2 virus corresponds to amino acid sequences with at least 75%, 80%, 85%, 90%, 95% or more identity with respect to the protein sequence the proteins N, E, M or S of SARS-CoV-2, defined as the product of the genes of the SEQ ID NO: 1, SEQ ID NO:2, SEQ ID NO:3 or SEQ ID NO:4, where the difference includes substitutions, deletions, additions or insertions. Likewise, for the person skilled in the art it will be evident that to obtain this protein expression the bacterium must be transformed with a vector containing a nucleotide sequence that encodes for said protein, where the invention includes a nucleotide sequence containing at least 75%, 80%, 85%, 90%, 95% or more identity with respect to the nucleotide sequence, defined according to SEQ ID NO:1, SEQ ID NO:2, SEQ ID NO:3 or SEQ ID NO:4 and their equivalents resulting from the degeneration of the genetic code.

For the expert in the art, it will be evident that in the case of variants of the SARS-CoV-2 virus, specific vaccines could be formulated, according to the peptide sequences of the viral proteins of these variants. Where, if said viral proteins of the SARS-CoV-2 variants have at least 75% identity with the sequences of the N, E, M or S proteins of SARS-CoV-2, defined as the product of the genes of the SEQ ID NO: 1, SEQ ID NO: 2, SEQ ID NO: 3 or SEQ ID NO: 4, those vaccines are considered within the scope of the present invention.

In an embodiment of the invention, the immunogenic formulation of the invention is stabilized by freezing, lyophilization or saline buffer and excipients for injectable preparations, for preservation prior to use. Among the appropriate excipients are: sodium glutamate, magnesium sulfate heptahydrate, potassium hydrogen phosphate, citric acid monohydrate, L-asparagine monohydrate, iron ammonium citrate, glycerol, and water for injections and any other available in the art, at the time. of executing the invention.

In another embodiment of the invention protects the use of the immunogenic formulation described to prepare a vaccine to prevent, treat or attenuate infections by SARS-CoV-2, wherein said formulation contains between $1\times10^4$-$1\times10^9$ CFU of the recombinant attenuated strain of *Mycobacterium bovis*, BCG, stabilized with a saline solution. This vaccine can be administered subcutaneously, percutaneously or subdermally in physiologically acceptable saline.

As we know, in many cases, COVID-19 vaccines require a booster after the first inoculation. In the case of the invention, it is proposed that said booster, within one to six months of the first inoculation, is performed with an attenuated virus vaccine, or purified viral subunits, or with peptide immunogenic fragments, or with DNA vaccine or even with RNA vaccine.

The booster with the vaccine of the invention can be applied some years after the first inoculation with the BCG vaccine, which would be performed, for example at the time of birth of infants.

To generate the formulation that is protected in this invention, the Danish or Pasteur strain of BCG is used, and we transform it at the genome level, expressing the N, E, M or S proteins of SARS-CoV-2 constitutively during its replicative cycle. The synthesis of this protein does not generate alterations or impediments in the replicative capacity of the bacterium, so it would not exert a toxicity effect on the vector strain.

Two characteristics to highlight of this invention correspond to its safety profile and immunogenicity, which we have evaluated in a preclinical murine model. Our results of growth curves and clinical manifestations in immunized mice indicate that the administration of this vaccine does not generate significant adverse reactions, having an effect similar to that of untransformed BCG or WT (for its acronym in English, wild type). With regard to the immunogenicity of this vaccine, we have observed that it generates a proliferation and activation of $CD4^+$ and $CD8^+$ specific T cells against the purified antigen N, E, M or S of SARS-CoV-2, essential stimuli to produce an immune response and generate immunological memory.

The safety and immunogenicity profile observed for the vaccine of the present invention make it a safe immunization tool.

There is currently no effective vaccine or treatment approved for the prevention or treatment of SARS-CoV-2 infection specific to the infant population and that can be applied from the time of birth. The recombinant BCG vaccine expressing the protein N, E, M and/or S SARS-CoV-2 according to the present invention can be used in individuals of all ages, including neonates. The invention consists of a vaccine developed in order to prevent COVID-19. BCG is a good vehicle for vaccine development as it has been shown to be safe in neonates, children and adults. It can be easily produced on a large scale with low costs and is stable to temperature changes. In addition, BCG acts as an adjuvant and induces Th1 responses (T helper lymphocyte), which are necessary for the elimination of the virus. Unlike other formulations, the BCG vector, in which the viral protein is expressed, has been widely used for almost 100 years in humans.

In one embodiment the vaccine comprises between $1\times10^4$-$1\times10^9$ CFU of a rBCG strain expressing the protein N, E, M and/or S of SARS-CoV-2, with at least 75%, 80%, 85%, 90%, 95% or more identity with respect to the peptide sequence of the products of the genes of the SEQ ID NO: 1, SEQ ID NO: 2, SEQ ID NO: 3 or SEQ ID NO:4.

In a second embodiment the vaccine comprises between $1\times10^4$-$1\times10^9$ CFU of a combination of two strains rBCG according to the invention wherein each strain rBCG expresses the protein N, E, M or S of SARS-CoV-2, with at least 75%, 80%, 85%, 90%, 95% or more identity with respect to the peptide sequence of the products of the genes of the SEQ ID NO: 1, SEQ ID NO: 2, SEQ ID NO:3 or SEQ ID NO:4., respectively. Where the combination is chosen among all possible alternatives, that is, transformed strains with any of the possible pairs: N and E; N and M; N and S; E and M; E and S; M and S.

In a third embodiment the vaccine comprises between $1\times10^4$-$1\times10^9$ CFU of a combination of three rBCG strains according to the invention wherein each rBCG strain expresses the protein N, E, M or S of SARS-CoV-2, with at least 75%, 80%, 85%, 90%, 95% or more identity with respect to the peptide sequence of the gene products of the SEQ ID NO: 1, SEQ ID NO:2, SEQ ID NO:3 or SEQ ID NO:4, respectively. Where the combination is chosen among all possible alternatives, that is, transformed strains with any of the possible trios: N, E and M; N, E and S; M, E and S; N, M and S.

In a fourth embodiment the vaccine comprises between $1\times10^4$-$1\times10^9$ CFU of a combination of the four rBCG strains according to the invention wherein each rBCG strain expresses the protein N, E, M or S of SARS-CoV-2, with at least 75%, 80%, 85%, 90%, 95% or more identity with respect to the peptide sequence of the products of the genes of the SEQ ID NO: 1, SEQ ID NO: 2, SEQ ID NO:3 or SEQ ID NO:4. That is, the combination of transformed strains with N, E, M and S.

The vaccines of the invention contain live attenuated recombinant strains of *Mycobacterium bovis*, preferably *Bacillus* Calmette-Guerin (BCG), for example the BCG Danish or Pasteur strains that express in a recombinant or heterologous manner one or more proteins or immunogenic fragments of SARS-CoV-2, especially the N protein or its immunogenic fragments. The vaccines of the invention comprise between $1\times10^4$-$1\times10^9$ CFU (colony forming units) of the strains described per dose, and can be kept preserved, prior to administration, lyophilized or in a saline solution and cold stabilizing excipients.

Examples of suitable stabilizing solutions for immunogenic formulations or vaccines of the invention are:

Diluted Sauton SSI solution (125 μg MgSO4, 125 μg K2HPO4, 1 mg L-asparragine, 12.5 μg ferric ammonium citrate, 18.4 mg 85% glycerol, 0.5 mg citric acid, in 1 ml $H_2O$) at 4° C.;

PBS (137 mM NaCl; 2.7 mM KCl; 4.3 mM Na2HPO4; 1.47 mM KH2PO4, pH 7,4) suplementado con Tween 80 0,02% y Glicerol 20% a −80° C.; or Volume solution: volume of lactose 25% and Proskauer and Beck medium supplemented with glucose and Tween 80 (PBGT: 0.5 g asparragine; 5.0 g monopotassium phosphate; 1.5 g magnesium citrate; 0.5 g potassium sulphate; 0.5 ml Tween 80 and 10.0 g glucose per litre of distilled water) lyophilised and stored in the temperature range between 4° C. and 25° C.

To obtain the recombinant strains of the invention, the genes that code for the N, E, M or S protein of SARS-CoV-2 or its immunogenic fragments, are inserted into a plasmid, which is incorporated into the bacterium by any available technique. In one embodiment, the plasmid pMV361 is used, incorporated into the bacterium by electroporation, and integrated into the bacterial genome by the action of integrases of mycobacteriophages. These genes can also be inserted into extrachromosomal plasmids, such as pMV261, which is incorporated into *Mycobacterium* by electrotransformation, and is maintained extrachromosomromously in the bacterium. These genes can be in one or more copies, and their expression is commanded by endogenous promoters of BCG, constitutive or inducible, for example the promoter of the hsp60 gene and the promoter of the acr gene respectively. These proteins, or immunogenic fragments of SARS-CoV-2, can be expressed by BCG or other attenuated strains of *Mycobacterium*, in a soluble-cytoplasmic manner, secreted extracellularly, or as membrane-bound proteins.

The formulations of the invention can be used to prepare a vaccine to prevent, treat, or attenuate infections of SARS-CoV-2 and/or the development of COVID-19 disease, wherein said formulation contains between $1\times10^4$-$1\times10^9$ colony forming units of the recombinant attenuated strain of *Mycobacterium bovis* BCG stabilized with a physiologically acceptable saline solution. Where said vaccine can be administered subcutaneously, percutaneously or subdermally in physiologically acceptable saline.

As is known from vaccines currently available on the market, SARS-CoV-2 vaccines often require a second dose one month after the first inoculation and booster doses with semi-annual or annual inoculations will likely continue to be required each winter, as is required for other persistent or seasonal illnesses, such as influenza.

In the case of vaccines of the invention, it should be considered that the current booster with BCG has been carried out at 5 years of life, and given the bivalence of the vaccine, since it continues to prevent tuberculosis, in addition to COVID-19, it is possible that in a vaccination schedule for newborns or young children, it is most convenient that the first booster for COVID-19, between one to six months from the inoculation with the vaccines of the invention, is made with some other existing vaccine on the market.

However, for annual boosters, or more spaced in time, of course it would be convenient to apply the formulations of the invention as boosters.

Among the vaccines that could be applied as a first booster between month 1 to 6 months from the first application, there are vaccines based on inactivated SARS-CoV-2 virus, or purified SARS-CoV-2 viral subunits, or with peptide immunogenic fragments of SARS-CoV-2, or with SARS-CoV-2 DNA vaccine or with RNA vaccine for SARS-CoV-2.

EXAMPLES

These examples are only illustrative and are not intended to limit the range of production or application of the invention. Although specific terms are used in the following descriptions, their use is only descriptive and not limiting.

Example I: Recombinant Danish BCG Strains for the N, E, M or S Gene of SARS-CoV-2

Four expression vectors were constructed for BCG containing the genes for the SARS-CoV-2 proteins N, E, S and M. For this, the plasmid pMV361 was used, which integrates only once into the genome of the bacterium.

To insert each gene into the plasmid, the combination of enzymes BstBI (TTCGAA) at the 5' end of each gene and ClaI at the 3' end (ATCGAT), for the N, E and M genes, were used. The sequence that is inserted into the plasmid to express protein N, is described in SEQ ID NO: 1. The one that is inserted into the plasmid to express protein E, is described in SEQ ID NO: 2, and the one that is inserted into the plasmid to express protein M, is described in SEQ ID NO: 3.

To insert the gene of Spike, S, the combination of enzymes MfeI (CAATTG) at the 5' end and Aflll at the 3' end of the gene (CTTAAG) was used, which was cloned in the pMV361 vector using the Gibson Assembly technique. The expression is described in SEQ ID NO. 4:

The plasmids obtained are called pMV361/N SARS-CoV-2, pMV361/E SARS-CoV-2, pMV361/M SARS-CoV-2 and pMV361/S SARS-CoV-2 respectively, and the inserted sequences are expressed under the control of an endogenous promoter and constitutive of the BCG hsp60 gene. Additionally, the plasmid has a gene for resistance to Kanamycin in order to select the transformed bacteria.

In order to verify that the plasmids contain the inserted segment, each of the inserts were cleaved from the plasmids, and it was verified by electrophoresis that the fragments obtained have the expected sizes in each case, this is a size of 226 bp for the E gene, a size of 669 bp for the M gene, a size of 1,260 bp for the N gene, a size of 4122 bp for the S1/S2 gene.

Once plasmids were obtained for each SARS-CoV-2 protein, electrocompetent BCGs were transformed with integrative expression plasmids expressing SARS-CoV-2 N, E, M and S-proteins.

With the plasmids obtained proceeded to independently transform cultures of a strain BCG electrocompetent Danish by electroporation with each plasmid pMV361/N SARS-CoV-2, pMV361/E SARS-CoV-2, pMV361/M SARS-CoV-2 and pMV361/S SARS-CoV-2.

The recombinant colonies resulting from the transformation were grown independently for 21 days at 37° C. in Middlebrock 7H9 culture medium supplemented with Kanamycin 25 ug/mL as a selection antibiotic.

The cultures were grown to $OD_{600nm}$=1 and the BCG transformed with the plasmids pMV361/N SARS-CoV-2, pMV361/E SARS-CoV-2, or pMV361/M SARS-CoV-2 and pMV361/S SARS-CoV-2 were centrifuged at 11,000 rpm for 20 min (Eppendorf rotor model 5702/R A-4-38) and resuspended in PBS solution (137 mM NaCl; 2.7 mM KCl; 4.3 mM $Na_2HPO_4$; 1.47 mM $KH_2PO_4$, PH 7.4).

Example II: Demonstration of Identity of Recombinant BCG Strains for the N, E, M or S Gene of SARS-CoV-2

Different tests were carried out to ensure the identity of each of the transformants obtained in example I. First, isolated colonies were obtained for each transformant in plates with 7H10 culture medium supplemented with Kanamycin.

Initially, we sought to verify that the microorganisms are indeed BCG, for which the presence of a fragment of 16S BCG and a fragment of the IS6610 insertion sequence in the culture was evaluated by PCR, which are only present in this type of bacteria and not in fungi or other types of microorganisms that could contaminate the culture. By amplification of these genes conserved in the BCG genome by PCR, and subsequent visualization in a 3% agarose gel, it was successfully confirmed that a set of colonies obtained after transformation with the recombinant plasmids pMV361/N SARS-CoV-2, pMV361/E SARS-CoV-2, or pMV361/M SARS-CoV-2 and pMV361/S SARS-CoV-2 corresponds to BCG.

Figure 1A:
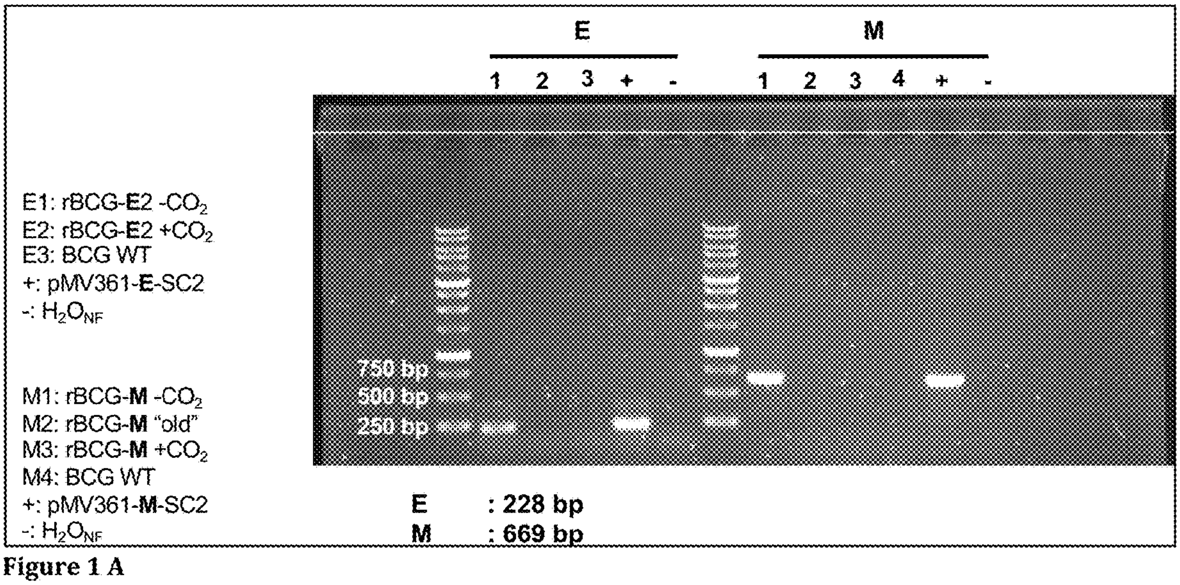
FIG. 1. A. Identification of recombinant BCG clones for E-SARS-CoV-2 and M-SARS-CoV-2 genes by PCR, using specific splitters. The identification of the genes of interest in the genome of the recombinant BCG strains was carried out using the specific primers for each of the genes of interest. Subsequently, the amplicon was analyzed in a 1% agarose gel, identifying amplicons of the expected size (228 bp for E-SARS-CoV-2 and 669 bp for M-SARS-CoV-2). "—$CO_2$" means that the bacteria were grown in the absence of CO2 5%. "+$CO_2$" means that the bacteria were grown in the presence of $CO_2$ 5%. "SC-2" is short for SARS-CoV-2. "Beta" means that it corresponds to a strain isolated in a previous trial and that remained in growth for 40 days, which was negative for M-SARS-CoV-2.
Figure 1B:
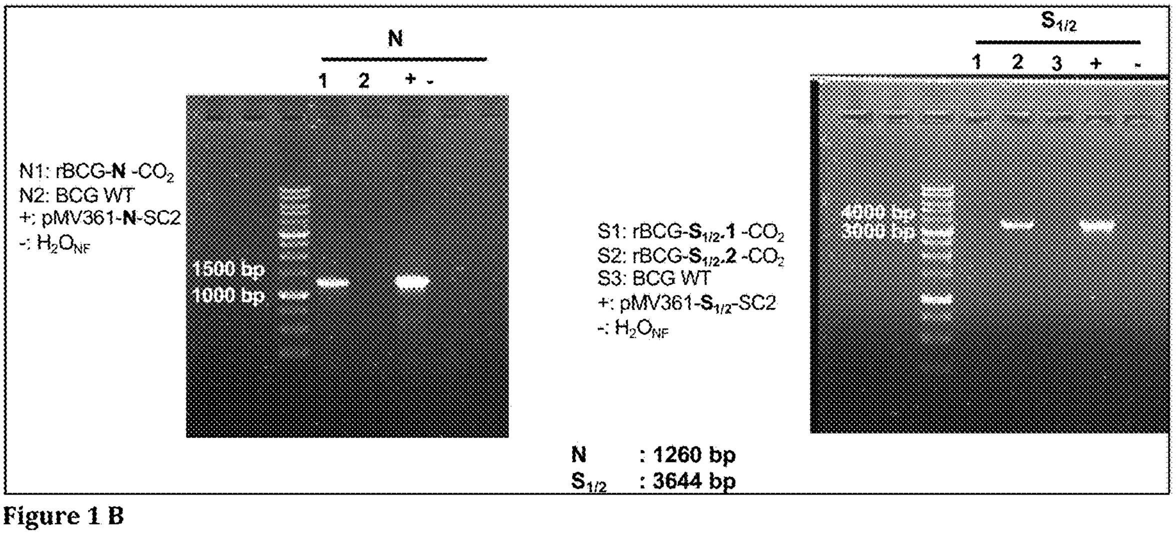

Secondly, the presence of the gene that codes for each SARS-CoV-2 protein of interest in the transformed strains was evaluated. This was done through a PCR with specific splitters for each viral gene N, E, M and/or S, for the corresponding strain. The results are shown in FIG. 1, where it is observed that in lanes "1" a band similar to the positive control "+" is obtained.

A fraction of recombinant BCGs obtained was subjected to a protein extraction protocol to evaluate the presence and expression of recombinant N, E, M and/or S antigens in each. To do this, these BCGs were resuspended in a lysis buffer (Tris 50 mM, EDTA 5 mM, SDS 0.6%, 1× protease inhibitor cocktail), subjected to 6 sonication pulses of 30 sec on ice with a rest pulse of 30 seconds.

The protein fraction of each transformed strain was analyzed by electrophoresis, comparing the proteome of each strain with the protein isolated from the corresponding virus, the photograph of the gel is shown in FIG. 2. It can be observed that in each case there are proteins of the molecular weight expected to the viral protein with which the BCG was transformed.

To determine if it is indeed viral proteins, immunological tests were performed, with murine monoclonal antibodies that specifically recognize the E, M, N, or S proteins of SARS-CoV-2. Subsequently, anti-mouse goat antibodies (Goat anti-mouse IgG-HRP), labeled with HRP, were used, which allows a colorimetric reaction. Western blot and Dot Blot tests were performed, and in both cases the results were positive for the corresponding viral protein for each transformed BCG pMV361/N SARS-CoV-2, pMV361/E SARS-CoV-2, pMV361/M SARS-CoV-2 or pMV361/S SARS-CoV-2.

Example III: Evaluation of Expression of Viral Proteins N, E, M and/or S of SARS-CoV-2 in Recombinant BCG Strains To complete the characterization of the recombinant strains of BCG, in addition to the identification of the gene by PCR, and confirmation of the expression of the protein inserted by Western blot and Dot blot, the quantification of the transcript or mRNA generated by the viral proteins of SARS-CoV-2 in the vaccine strain of the invention was performed by the qPCR technique (quantitative).

Using this methodology, it was possible to find that all clones of rBCG-N-SARS-CoV-2, E-SARS-CoV-2, M-SARS-CoV-2 and S-SARS-CoV-2 express the gene of interest, which can be seen in FIG. 3. With this analysis, it is intended to estimate the amount of protein that the vaccine strain could be expressing. With this information, test doses can be estimated for future animal immunization trials.

Figure 3A:
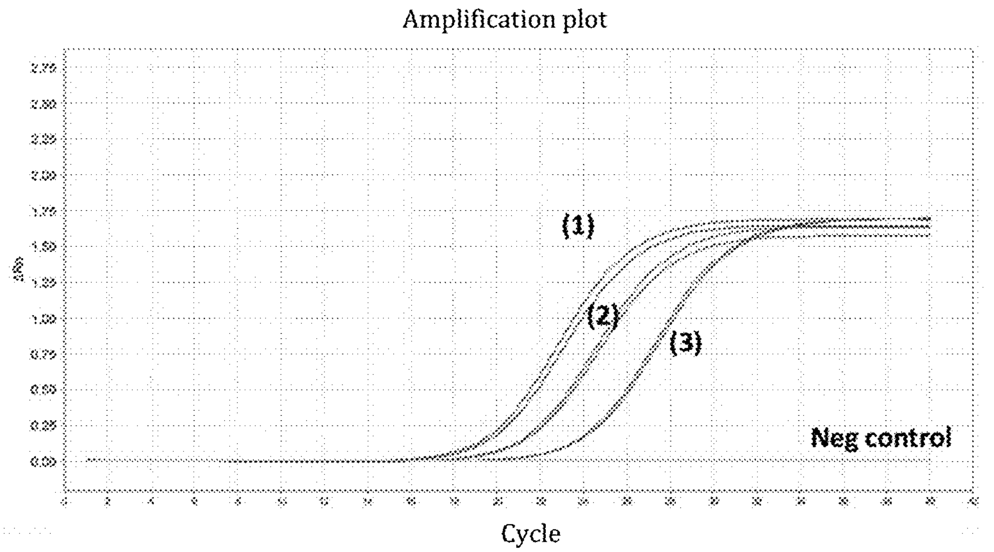
Figure 3B:
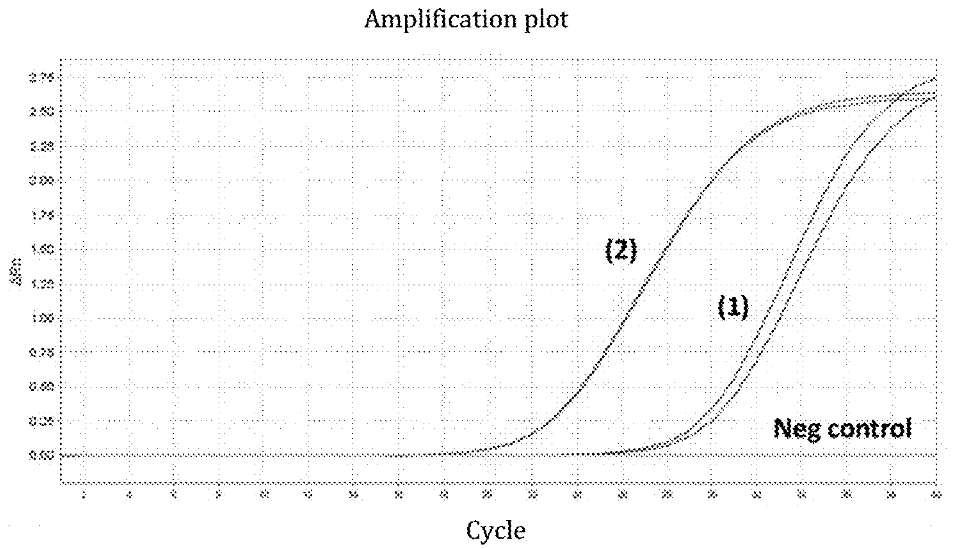
Figure 3C:
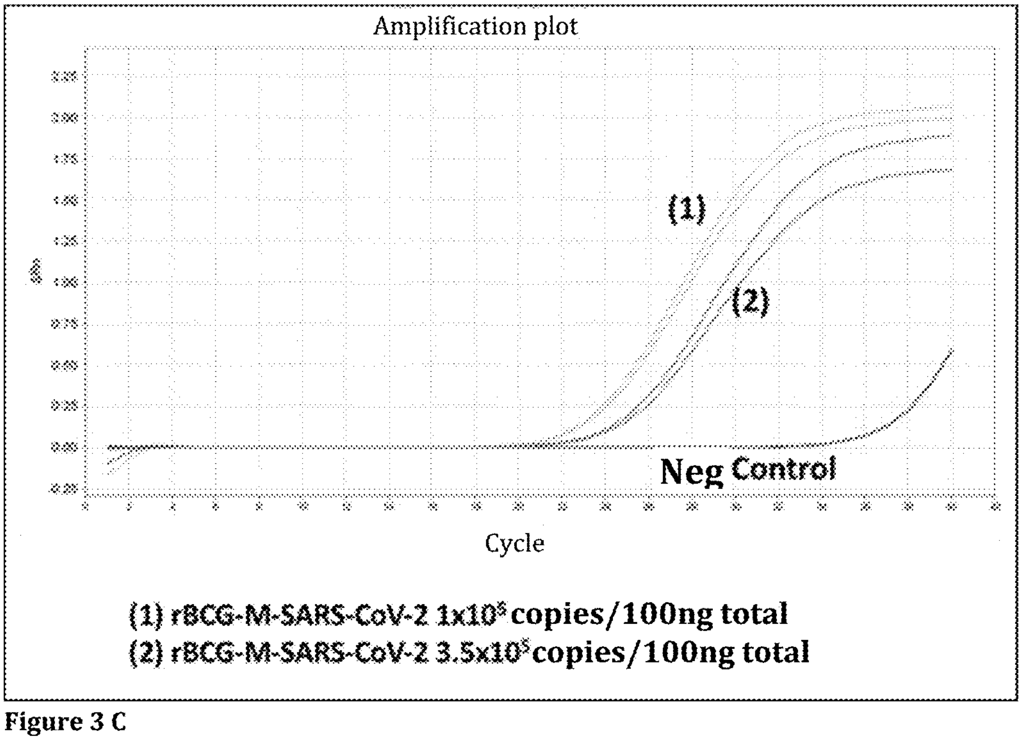
Figure 3D:
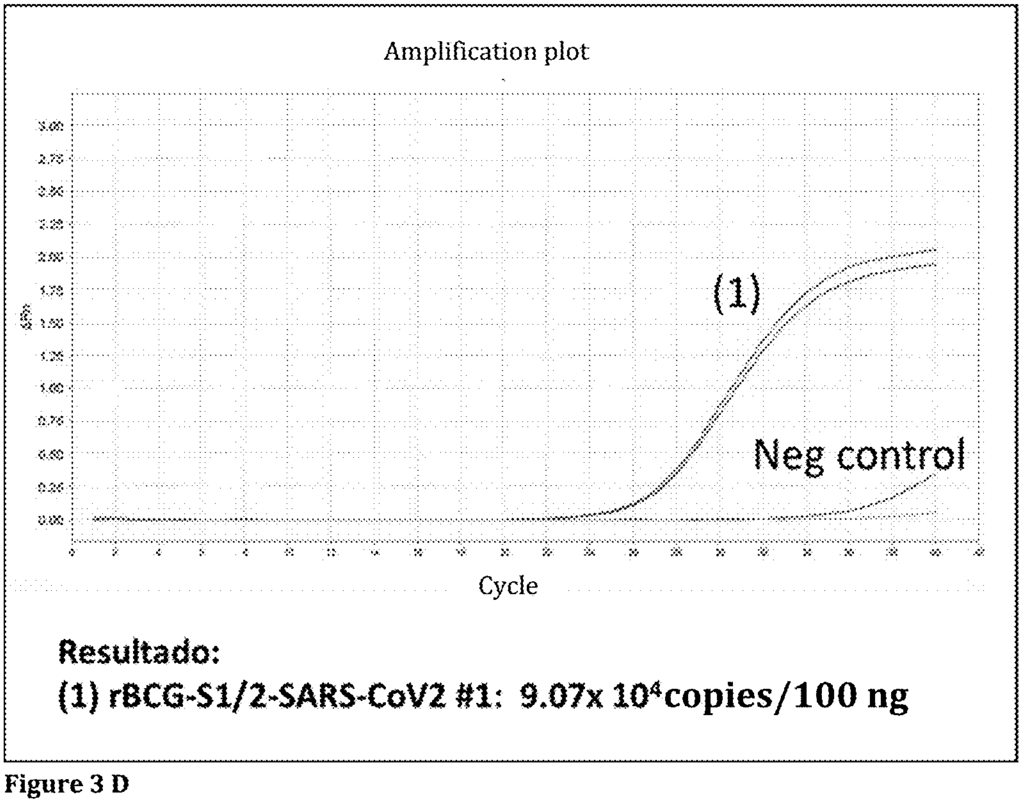

The number of transcripts for the N-SARS-CoV-2 gene in 2 clones of rBCG-N-SARS-CoV-2 was evaluated, the results are shown in FIG. 3A. During the first passage of culture, clone 2 presented a greater number of copies of the transcript. However, when this was evaluated with a sample of RNA obtained from clone 1 culture passage 2, an increase of an order of magnitude was observed in the amount of transcript with respect to that obtained in the first passage.

The same assay was performed to evaluate the number of transcripts for the E-SARS-CoV-2 gene, observing the presence of the copy number for the gene evaluated for the two passages of the culture evaluated (FIG. 3 B). However, it was determined that the amount of transcript obtained in the second passage of culture of the strain rBCG-E-SARS-CoV-2 was higher by three orders of magnitude with respect to the amount obtained during the first passage of the culture.

The expression of the M-SARS-CoV-2 gene was also evaluated with the same methodology mentioned for the other genes. From this trial it was observed that the presence of the copy number for the M-SARS-CoV-2 gene evaluated for the two passages of the culture was similar (FIG. 3 C).

Finally, the conditions were standardized to detect the expression of protein S (Spike) in the recombinant strain of BCG. When the first culture passage of this vaccine strain was evaluated, it was obtained that the expression was present, however, the number of copies was not very high (FIG. 3 D).

Example IV: Immunogenic Formulation

The resulting recombinant colonies in the previous example transformed with pMV361/N SARS-CoV-2, pMV361/E SARS-CoV-2, pMV361/S SARS-CoV-2 or pMV361/M SARS-CoV-2, were grown at 37° C. in culture medium Middlebrock 7H9 supplemented, with Kanamycin 25 ug/ml as a selection antibiotic up to $OD_{600nm}$=1, were centrifuged at 11,000 rpm for 20 min (eppendorf rotor model 5702/R A-4-38) and resuspended in PBS solution (137 mM NaCl; 2.7 mM KCl; 4.3 mM $Na_2HPO_4$; 1.47 mM $KH_2PO_4$, pH 7.4).

To generate doses of vaccine of specific concentration, for example $10^5$ or $10^8$ CFU per 100 μl, serial dilutions were carried out in plates with 7H9 medium, performing colony counting, from the dose vials. The presence of contaminants was ruled out by seeding some of the doses in LB and 7H9 plates without antibiotics. Finally, once it was confirmed that the doses were accurate with respect to the number of CFUs, they were stored at −80° C. until their use as a vaccine in animals.

Doses of recombinant BCG were generated for protein N, E, M and/or S of SARS-CoV-2, where BCG strains were transformed with plasmids containing the sequences indicated in SEQ ID NO:1 for N, SEQ ID NO: 2 for E, SEQ ID NO:3 for M or SEQ ID NO:4 for S1/S2 and identified as rBCG-N-SARS-CoV-2, rBCG-E-SARS-CoV-2, rBCG-M-SARS-CoV-2 and rBCG-S-SARS-CoV-2.

Doses may contain only one of the transformed bacteria, or a combination of 2 of them, or a combination of 3 of them or all 4, where in each combination of more than one transformed bacterium each may be present in any proportion. That is, a dose can contain between 0 to 100% rBCG-E-SARS-CoV-2, between 0 to 100% rBCG-M-SARS-CoV-2, between 0 to 100% rBCG-N-SARS-CoV-2 and between 0 to 100% rBCG-S-SARS-CoV-2.

The doses thus prepared can be used to vaccinate animals by subcutaneous or percutaneous or subdermal injection.

Example V: Immunisation of Animals with an rBCG Strain 2 sets of immunization tests were performed in animal model (mouse), with the compositions obtained in example IV. The experimental design was developed to evaluate cellular and humoral immunity induced by vaccination with a recombinant BCG strain expressing either SARS-CoV-2 E, N, M and/or S protein.

The first set of analyses was performed according to the diagram in FIG. 4, with 2 vaccinations of the animals on days 0 and 14 with a dose of $1\times10^8$ CFU. Blood samples were taken at 7, 14 and 21 days, where on day 21 the experiment was ended with euthanasia of the animals.

The second set of analyses was performed according to the scheme in FIG. 5, with 1 vaccination of the animals on day 0 with a dose of $1\times10^5$ CFU. Blood samples were taken at 7, 14 and 21 days, where on day 21 the experiment was ended with euthanasia of the animals.

In each case the doses of CFU correspond to the transformed BCG of the invention, which correspond to transformed BCG pMV361/N SARS-CoV-2, pMV361/E SARS-CoV-2, pMV361/M SARS-CoV-2 or pMV361/S SARS-CoV-2.

Example VI: Effect of Vaccine with an rBCG Strain in Animals

To evaluate the effect of vaccination with the strain rBCG-N-SARS-CoV-2 in both immunization schemes developed in the previous example, we proceeded to generate a co-culture between dendritic cells (DCs) loaded with different peptides and treatments, and purified T lymphocytes from secondary lymphoid organs of vaccinated animals (spleen and lymph nodes), for 72 hours. After this time the cells were stained with different antibodies to evaluate the activation of these T lymphocytes. Additionally, the activation markers $CD69^+$, $CD71^+$ and $CD25^+$ were evaluated on the surface of $CD4^+$ and $CD8^+$ T lymphocytes by flow cytometry. In addition, cytokines were evaluated by ELISA from the supernatants of the co-cultures.

From the co-culture from the second immunization scheme, cytokines were evaluated in the supernatants of the different treatments. Initially, the cytokines IL-2 and IFN-gamma were evaluated. IL-2 was evaluated to correlate an increase in T cell proliferation, while IFN-gamma was evaluated to correlate the immune response promoted by the vaccine.

When IFN-gamma was evaluated, it was determined that animals vaccinated with the rBCG-N-SARS-CoV-2 strain promote better secretion of this cytokine that polarizes the immune response to an antiviral profile, see FIG. 6.

To evaluate whether vaccination with the rBCG-N-SARS-CoV-2 strain induces a cellular immune response, after ending the experiment, total T lymphocytes were purified from the spleens from the second immunization schedule. These were then co-cultured with dendritic cells loaded with different peptides and treatments for 72 hours. After this time, the activation markers $CD69^+$, $CD71^+$ and $CD25^+$ were evaluated on the surface of $CD4^+$ and $CD8^+$ T lymphocytes by flow cytometry.

The results are shown in FIG. 7, where it can be seen that T lymphocytes are specifically activated in response to the SARS-CoV-2 N protein (20 μg). The result is very noticeable for all the evaluated $CD4^+$ and T $CD8^+$ lymphocytes, the response against the specific viral antigen is similar to the response against the positive control Concanavalina A (With A).

These results are very important, as it implies that the vaccine has a positive effect on promoting $CD4^+$ T lymphocytes, which can help activate the immune response against the virus, and at the same time promoting $CD8^+$ T lymphocytes that have an antiviral effect.

In addition to these results, the observed cellular response was complemented with the measurement of antibodies induced for both immunization schedules. From the immunization schedule with two doses of $1\times10^8$ CFU showed an efficient induction of anti-N-SARS-CoV-2 antibodies by ELISA, 24 days after immunization. From the data obtained it was possible to identify that the vaccine strain rBCG-N-SARS-CoV-2 is capable of promoting a mild antibody response prior to the stimulus, observing a small increase at day 14 for the bar indicated with *. However, this increase is much more noticeable after the stimulus at day 24 where it is observed that there is a high response to the stimulus from the sera of animals vaccinated with the recombinant strain rBCG-N-SARS-CoV-2 (FIG. 8).

Example VII: Immunisation of Animals with Mixtures of rBCG Strains

A set of immunization tests was performed in animal model (mouse), with the compositions obtained in example IV, comprising a mixture of the four transformed strains (25% rBCG-E-SARS-CoV-2, 25% rBCG-M-SARS-CoV-2, 25% rBCG-N-SARS-CoV-2 and 25% rBCG-S-SARS-CoV-2). The experimental design was developed to evaluate cellular and humoral immunity induced by vaccination with a formulation of the invention.

To carry out this, an immunization was performed with a dose of $4\times10^5$ total CFU ($1\times10^5$ CFU of each of the recombinant strains of the invention), after 14 days the animals were subjected to a second immunization that corresponded to a booster using purified proteins E, M, N and S, 40 μg in total, (10 μg of each) administered in the company of aluminum hydroxide adjuvant, the scheme of the experiment is in FIG. 9. Blood samples were taken at 0, 14 and 24 days after immunization, where on day 24 the experiment was ended with the euthanasia of the animals.

Additionally, different controls were included, each in a group of 3 animals, as indicated in Table 1.

TABLE 1

| Group | 1st vaccination | Booster |
|---|---|---|
| Control | PBS | PBS |
| Control BCG | BCG-WT | PBS |
| Control BCG, Alum | BCG-WT | Alum |
| Invention, 1 dose | rBCG-pool | PBS |
| Invention, 1 dose and protein booster | rBCG-pool | rProteínas + Alum |
| Control booster | PBS | rProteínas + Alum |
| Control Alum | PBS | Alum |

Example VIII: Effect of Vaccine with Mixtures of rBCG Strains in Animals

First, the evaluation of weight loss of animals subjected to the vaccination scheme of the invention and its controls was carried out, where the vaccine of the invention corresponds to a pool or mixture of the 4 recombinant strains of BCG together. The results are shown in FIG. 10. The vaccination scheme of the invention proved to be safe, since the animals did not decrease their weight over time.

From the blood samples obtained on days 0, 14 and 24, the determination of antibodies against the N protein of the SARS-CoV-2 virus was performed, observing that vaccination with the BCG pool promotes an increase in anti-N-SARS-CoV-2 antibodies in animals, greater than that obtained in all control groups. It was observed that this effect was ostensibly greater at the end of the trial (day 24) in the group corresponding to the invention, immunized with the pool of recombinant strains and with the booster constituted by a mixture of recombinant proteins (N, M and S) and Alum. The antibodies present in the sera obtained from the test animals were evaluated by the ELISA technique, using recombinant protein N (rN) of SARS-CoV-2 as a target and anti-mouse antibodies bound to the enzyme HRP, which gives the colorimetric reaction. The sera of the study animals diluted ⅕ was used. The colorimetric reaction was evaluated in an ELISA reader at a wavelength of 450 nm. The results are shown in FIG. 11, where it can be seen that the best production of anti-N antibodies is obtained with the vaccination scheme of the invention, on day 24 of the experiment.

Additionally, a titration was performed to determine whether the immunization schemes of the invention had allowed animals to develop antibodies against the S protein of the SARS-CoV-2 virus. For this, the sera obtained on day 24 of the trial were used, where a measurement was made for each group of animals, using a mixture in equal proportions of the sera from the 3 animals that make up each experimental group. From this trial, it was possible to determine that vaccination performed using the vaccination scheme of the invention promotes a strong antibody response against the S protein of SARS-CoV-2. Where the production of antibodies is notoriously higher in the scheme of the invention, with respect to what was observed for the rest of the experimental groups, as shown in FIG. 12. In particular, the results show that the combination of the pool of strains of the invention with a booster of a pool of viral recombinant proteins (N, M and S) generate significantly more antibodies than the use only of the strains of the invention (pool) and the use only of recombinant proteins.

Since it was shown that the scheme of the invention promotes the generation of antibodies against the SARS-CoV-2 virus, the cellular immune response was also evaluated, evaluating the activation of $CD8^+$ T lymphocytes, of antiviral effect. For this, after putting an end to the experiment, on day 24, total T lymphocytes were purified from the spleens of the animals. The conditions evaluated are summarized in Table 2.

TABLE 2

| Sample | 1st vaccination | Booster |
|---|---|---|
| Control BCG | BCG-WT | PBS |
| Invention, 1 dose | rBCG-pool | PBS |
| Invention, 1 dose and protein booster | rBCG-pool | rProteínas + Alum |
| Control booster | PBS | rProteínas + Alum |
| Control Alum | PBS | Alum |

The purified T lymphocytes were then co-cultured with dendritic cells loaded with different SARS-CoV-2 peptides for 72 hours, the peptides used correspond to the N, M and S proteins, or the mixture of N, M and S.

Figure 13:
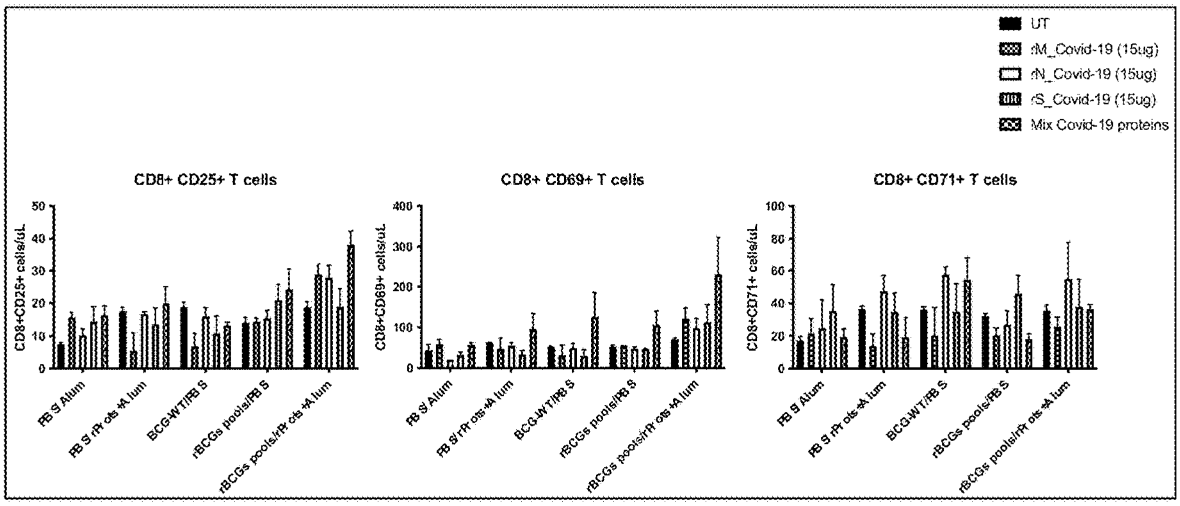

At the end of incubation, $CD69^+$, $CD71^+$ and $CD25^+$ activation markers on the surface of CD8+T lymphocytes were evaluated by flow cytometry. The results are shown in FIG. 13.

The results show that the different stimuli evaluated (N, M and S, or their mixture) effectively stimulate $CD8^+$ T lymphocytes, increasing the expression of the $CD69^+$, $CD71^+$ and $CD25^+$ markers. Specifically, a higher expression of the marker $CD69^+$ was found in the group with the vaccination scheme of the invention, "rBCGs pool/rProts+Alum", against the stimuli of the proteins M, N and for the mixture of proteins in the co-culture (FIG. 13 B). On the other hand, the second most expressed activation marker in the group of interest was $CD71^+$, mainly in response to S protein stimuli and protein mix (FIG. 13C). Finally, a response similar to that observed for $CD71^+$ in the expression of the $CD25^+$ marker was observed (FIG. 13A).

The data obtained in this study show that the use of a pool of recombinant BCG strains, which express the different SARS-CoV-2 proteins, promote a humoral and cellular immune response that would be effective against SARS-CoV-2 infection in a model without infection.

Example IX: Comparative Example: Vaccination Scheme of the Invention v/s Inactivated Virus Vaccine In order to establish comparatively the immunity granted by the vaccination scheme of the invention, an experiment was conducted where animals were immunized according to the invention and simultaneously with inactivated virus vaccines. The vaccination schedule is summarized in Table 3:

TABLE 3

| Group | 1st vaccination | Booster |
|---|---|---|
| Invention (3 animals) | 1 × $10^5$ CFU of rBCG-N-SARS-CoV-2 | recombinant N protein (10 ug) + Alum |
| Inactivated virus vaccine (6 animals) | 600 IU inactivated virus | 600 IU inactivated virus |
| Control (UI) (3 animals) | Untreated (PBS) | Untreated (PBS) |

Based on the immunization schedule in Table 3, we proceeded to evaluate the immune response induced by vaccination with our vaccine strain rBCG-N-SARS-CoV-2 compared to the response generated by vaccination with inactivated virus.

After finishing the experiment, the spleens and lymph nodes of the animals were collected and from these the purification of total T lymphocytes was performed. These lymphocytes were then co-cultured with dendritic cells previously loaded with the various stimuli for 72 hours. The treatments evaluated were negative or untreated control (UT), with SARS-CoV-2 N protein, and with purified protein derivative (PPD), which is used as a positive infection marker or positive BCG stimulation control, and the group immunized with inactivated virus also with SARS-CoV-2 S protein. The results are shown in FIG. 14, where it can be seen that after the vaccination schemes of the invention and with inactivated virus a similar activation of $CD8^+$ T lymphocytes is obtained, increasing the expression of markers $CD69^+$, $CD71^+$ and $CD25^+$.

Finally, the ability of both vaccines to promote the secretion of anti-N antibodies in the serum of the animals was evaluated. To determine this, the determination of total anti-N-SARS-CoV-2 antibodies present in the sera obtained from the animals at different times within the experiment was carried out using the indirect ELISA technique. The results show that once the vaccination schedule was completed, both groups, (invention and the group vaccinated with inactivated virus), stimulated the secretion of antibodies against SARS-CoV-2 N protein at similar levels (FIG. 15).

These results show that transformed BCG strains constitutively express SARS-CoV-2 proteins, so when used in an immunogenic formulation they would allow the individual (animal or person) receiving this composition to develop immunity against SARS-CoV-2, which would provide protection against COVID-19.

The invention claimed is:

1. An immunogenic formulation conferring protection against COVID-19, comprising:

(a) a mixture of attenuated recombinant strains of *Mycobacterium bovis Bacillus* Calmette-Guerin (BCG), wherein the mixture comprises:

a recombinant *Mycobacterium bovis* BCG strain expressing an N protein of a SARS-CoV-2 virus or an immunogenic fragment thereof, a recombinant *Mycobacterium bovis* BCG strain expressing an E protein of the SARS-CoV-2 virus or an immunogenic fragment thereof, a recombinant *Mycobacterium bovis* BCG strain expressing an M protein of the SARS-CoV-2 virus or an immunogenic fragment thereof, and a recombinant *Mycobacterium bovis* BCG strain expressing an S protein of the SARS-CoV-2 virus or an immunogenic fragment thereof, wherein each recombinant *Mycobacterium bovis* BCG strain is included in the immunogenic formulation in an amount from $10^4$ to $10^9$ CFU per dose; and (b) a pharmaceutically acceptable saline buffer solution.

2. The immunogenic formulation according to claim 1, wherein the N, the E, the M, and the S proteins of the SARS-CoV-2 virus, or the immunogenic fragments thereof, correspond to an amino acid sequence at least 75% identical to gene products of nucleotide sequences defined in SEQ ID NO: 1, SEQ ID NO: 2, SEQ ID NO: 3, and SEQ ID NO: 4, respectively.

3. The immunogenic formulation according to claim 1, wherein the N, the E, the M, and the S proteins of the SARS-CoV-2 virus, or the immunogenic fragments thereof, are at least 95% identical to gene products of nucleotide sequences defined in SEQ ID NO:1, SEQ ID NO:2, SEQ ID NO: 3, and SEQ ID NO:4, respectively.

4. The immunogenic formulation according to claim 2, wherein each of the genes that code for the N, the E, the M, and the S proteins of the SARS-CoV-2 virus or the immunogenic fragments thereof is inserted into a genome of *Mycobacterium bovis* BCG or into extrachromosomal plasmids, in one or more copies.

5. The immunogenic formulation according to claim 4, wherein the expression of the genes is commanded by a constitutive endogenous promoter of *Mycobacterium bovis* BCG.

6. The immunogenic formulation according to claim 5, wherein each of the N, the E, the M, or the S proteins of the SARS-CoV-2 virus or the immunogenic fragments thereof is configured to be expressed by the *Mycobacterium bovis* BCG in a soluble-cytoplasmic form, secreted extracellularly, or expressed as a protein bound to cell membrane.

7. The immunogenic formulation according to claim 1, wherein said immunogenic formulation is stabilized by freezing, lyophilizing, or being in saline buffer and excipients for preservation prior to being administered to an individual.

8. The immunogenic formulation according to claim 6, wherein said immunogenic formulation is stabilized by freezing, lyophilizing, or being in saline buffer and excipients for preservation prior to being administered to an individual.

9. The immunogenic formulation according to claim 1, wherein the attenuated recombinant strain is BCG Danish or BCG Pasteur.

10. The immunogenic formulation according to claim 1, wherein said immunogenic formulation comprises 25% each of the recombinant *Mycobacterium bovis* BCG strains expressing the N, the E, the M, and the S proteins of SARS-CoV-2 virus or immunogenic fragments thereof.

11. A method for treating SARS-CoV-2 infections, wherein the method comprises administering the immunogenic formulation of claim 1 to an individual in need thereof.

12. The method of claim 11, wherein said immunogenic formulation is administered subcutaneously, percutaneously, or subdermally, in physiologically acceptable saline.

13. The method of claim 12, wherein the method further comprises administering a booster after the administering the immunogenic formulation of claim 1, the booster comprising:

a formulation of the attenuated recombinant strain of *Mycobacterium bovis* BCG, in an amount from $10^4$ to $10^9$ CFU per dose, which expresses at least one protein or immunogenic fragment of the SARS-CoV-2 virus; or an immunogenic formulation of an inactivated SARS-CoV-2 virus; or an immunogenic formulation of a purified SARS-CoV-2 viral subunits; or an immunogenic formulation with peptide immunogenic fragments of SARS-CoV-2; or an immunogenic formulation of SARS-CoV-2 DNA vaccine; or an immunogenic formulation with RNA vaccine for SARS-CoV-2.

* * * * *

SEQUENCE LISTING

```
<160> NUMBER OF SEQ ID NOS: 4

<210> SEQ ID NO 1
<211> LENGTH: 1272
<212> TYPE: DNA
<213> ORGANISM: SARS-CoV-2

<400> SEQUENCE: 1
```

-continued ttcgaaatgt ctgataatgg accccaaaat cagcgaaatg caccccgcat tacgtttggt 60
ggaccctcag attcaactgg cagtaaccag aatggagaac gcagtggggc gcgatcaaaa 120
caacgtcggc cccaaggttt acccaataat actgcgtctt ggttcaccgc tctcactcaa 180
catggcaagg aagaccttaa attccctcga ggacaaggcg ttccaattaa caccaatagc 240
agtccagatg accaaattgg ctactaccga agagctacca gacgaattcg tggtggtgac 300
ggtaaaatga aagatctcag tccaagatgg tatttctact acctaggaac tgggccagaa 360
gctggacttc cctatggtgc taacaaagac ggcatcatat gggttgcaac tgagggagcc 420
ttgaatacac caaaagatca cattggcacc cgcaatcctg ctaacaatgc tgcaatcgtg 480
ctacaacttc ctcaaggaac aacattgcca aaaggcttct acgcagaagg gagcagaggc 540
ggcagtcaag cctcttctcg ttcctcatca cgtagtcgca acagttcaag aaattcaact 600
ccaggcagca gtaggggaac ttctcctgct agaatggctg gcaatggcgg tgatgctgct 660
cttgctttgc tgctgcttga cagattgaac cagcttgaga gcaaaatgtc tggtaaaggc 720
caacaacaac aaggccaaac tgtcactaag aaatctgctg ctgaggcttc taagaagcct 780
cggcaaaaac gtactgccac taaagcatac aatgtaacac aagctttcgg cagacgtggt 840
ccagaacaaa cccaaggaaa ttttggggac caggaactaa tcagacaagg aactgattac 900
aaacattggc cgcaaattgc acaatttgcc cccagcgctt cagcgttctt cggaatgtcg 960
cgcattggca tggaagtcac accttcggga acgtggttga cctacacagg tgccatcaaa 1020
ttggatgaca aagatccaaa tttcaaagat caagtcattt tgctgaataa gcatattgac 1080
gcatacaaaa cattcccacc aacagagcct aaaaaggaca aaaagaagaa ggctgatgaa 1140
actcaagcct taccgcagag acagaagaaa cagcaaactg tgactcttct tcctgctgca 1200
gatttggatg atttctccaa acaattgcaa caatccatga gcagtgctga ctcaactcag 1260
gcctaaatcg at 1272

<210> SEQ ID NO 2
<211> LENGTH: 240
<212> TYPE: DNA
<213> ORGANISM: SARS-CoV-2

<400> SEQUENCE: 2
ttcgaaatgt actcattcgt ttcggaagag acaggtacgt taatagttaa tagcgtactt 60
ctttttcttg ctttcgtggt attcttgcta gttacactag ccatccttac tgcgcttcga 120
ttgtgtgcgt actgctgcaa tattgttaac gtgagtcttg taaaaccttc tttttacgtt 180
tactctcgtg ttaaaaatct gaattcttct agagttcctg atcttctggt ctaaatcgat 240

<210> SEQ ID NO 3
<211> LENGTH: 681
<212> TYPE: DNA
<213> ORGANISM: SARS-CoV-2

<400> SEQUENCE: 3
ttcgaaatgg cagattccaa cggtactatt accgttgaag agcttaaaaa gctccttgaa 60
caatggaacc tagtaatagg tttcctattc cttacatgga tttgtcttct acaatttgcc 120
tatgccaaca ggaataggtt tttgtatata attaagttaa ttttcctctg gctgttatgg 180
ccagtaactt tagcttgttt tgtgcttgct gctgtttaca gaataaattg gatcaccggt 240
ggaattgcta tcgcaatggc ttgtcttgta ggcttgatgt ggctcagcta cttcattgct 300

```
tctttcagac tgtttgcgcg tacgcgttcc atgtggtcat tcaatccaga aactaacatt    360

cttctcaacg tgccactcca tggcactatt ctgaccagac cgcttctaga aagtgaactc    420

gtaatcggag ctgtgatcct tcgtggacat cttcgtattg ctggacacca tctaggacgc    480

tgtgacatca aggacctgcc taaagaaatc actgttgcta catcacgaac gctttcttat    540

tacaaattgg gagcttcgca gcgtgtagca ggtgactcag gttttgctgc atacagtcgc    600

tacaggattg gcaactataa attaaacaca gaccattcca gtagcagtga caatattgct    660

ttgcttgtac agtaaatcga t                                               681
```

<210> SEQ ID NO 4
<211> LENGTH: 3651
<212> TYPE: DNA
<213> ORGANISM: SARS-CoV-2

<400> SEQUENCE: 4

```
caattgatgt ttgtttttct tgttttattg ccactagtct ctagtcagtg tgttaatctt     60

acaaccagaa ctcaattacc ccctgcatac actaattctt tcacacgtgg tgtttattac    120

cctgacaaag ttttcagatc ctcagtttta cattcaactc aggacttgtt cttacctttc    180

ttttccaatg ttacttggtt ccatgctata catgtctctg ggaccaatgg tactaagagg    240

tttgataacc ctgtcctacc atttaatgat ggtgtttatt ttgcttccac tgagaagtct    300

aacataataa gaggctggat ttttggtact actttagatt cgaagaccca gtccctactt    360

attgttaata acgctactaa tgttgttatt aaagtctgtg aatttcaatt ttgtaatgat    420

ccatttttgg gtgtttatta ccacaaaaac aacaaaagtt ggatggaaag tgagttcaga    480

gtttattcta gtgcgaataa ttgcactttt gaatatgtct ctcagccttt tcttatggac    540

cttgaaggaa aacagggtaa tttcaaaaat cttagggaat ttgtgtttaa gaatattgat    600

ggttatttta aaatatattc taagcacacg cctattaatt tagtgcgtga tctccctcag    660

ggtttttcgg ctttagaacc attggtagat ttgccaatag gtattaacat cactaggttt    720

caaactttac ttgctttaca tagaagttat ttgactcctg gtgattcttc ttcaggttgg    780

acagctggtg ctgcagctta ttatgtgggt tatcttcaac ctaggacttt tctattaaaa    840

tataatgaaa atggaaccat tacagatgct gtagactgtg cacttgaccc tctctcagaa    900

acaaagtgta cgttgaaatc cttcactgta gaaaaaggaa tctatcaaac ttctaacttt    960

agagtccaac caacagaatc tattgttaga tttcctaata ttacaaactt gtgccctttt   1020

ggtgaagttt ttaacgccac cagatttgca tctgtttatg cttggaacag gaagagaatc   1080

agcaactgtg ttgctgatta ttctgtccta tataattccg catcattttc cacttttaag   1140

tgttatggag tgtctcctac taaattaaat gatctctgct ttactaatgt ctatgcagat   1200

tcatttgtaa ttagaggtga tgaagtcaga caaatcgctc cagggcaaac tggaaagatt   1260

gctgattata attataaatt accagatgat tttacaggct gcgttatagc ttggaattct   1320

aacaatcttg attctaaggt tggtggtaat tataattacc tgtatagatt gtttaggaag   1380

tctaatctca aacctttga gagagatatt tcaactgaaa tctatcaggc cggtagcaca    1440

ccttgtaatg gtgttgaagg ttttaattgt tactttcctt tacaatcata tggtttccaa   1500
```

-continued

```
cccactaatg gtgttggtta ccaaccatac agagtagtag tactttcttt tgaacttcta   1560
catgcaccag caactgtttg tggacctaaa aagtctacta atttggttaa aaacaaatgt   1620
gtcaatttca acttcaatgg tttaacaggc acaggtgttc ttactgagtc taacaaaaag   1680
tttctgcctt tccaacaatt tggcagagac attgctgaca ctactgatgc tgtccgtgat   1740
ccacagacac ttgagattct tgacattaca ccatgttctt ttggtggtgt cagtgttata   1800
acaccaggaa caaatacttc taaccaggtt gctgttcttt atcaggatgt taactgcaca   1860
gaagtccctg ttgctattca tgcagatcaa cttactccta cttggcgtgt ttattctaca   1920
ggttctaatg tttttcaaac acgtgcaggc tgtttaatag gggctgaaca tgtcaacaac   1980
tcatatgagt gtgacatacc cattggtgca ggtatatgcg ctagttatca gactcagact   2040
aattctcctc ggcgggcacg tagtgtagct agtcaatcca tcattgccta cactatgtca   2100
cttggtgcag aaaattcagt tgcttactct aataactcta ttgccatacc cacaaatttt   2160
actattagtg ttaccacaga aattctacca gtgtctatga ccaagacatc agtagattgt   2220
acaatgtaca tttgtggtga ttcaactgaa tgcagcaatc ttttgttgca atatggcagt   2280
ttttgtacac aattaaaccg tgctttaact ggaatagctg ttgaacaaga caaaaacacc   2340
caagaagttt ttgcacaagt caaacaaatt tacaaaacac caccaattaa agattttggt   2400
ggttttaatt tttcacaaat attaccagat ccatcaaaac caagcaagag gtcatttatt   2460
gaagatctac ttttcaacaa agtgacactt gcagatgctg gcttcatcaa acaatatggt   2520
gattgccttg gtgatattgc tgctagagac ctcatttgtg cacaaaagtt taacggcctt   2580
actgttttgc cacctttgct cacagatgaa atgattgctc aatacacttc tgcactgtta   2640
gcgggtacaa tcacttctgg ttggaccttt ggtgcaggtg ctgcattaca aataccattt   2700
gctatgcaaa tggcttatag gtttaatggt attggagtta cacagaatgt tctctatgag   2760
aaccaaaaat tgattgccaa ccaatttaat agtgctattg gcaaaattca agactcactt   2820
tcttccacag caagtgcact tggaaaactt caagatgtgg tcaaccaaaa tgcacaagct   2880
ttaaacacgc ttgttaaaca acttagctcc aattttggtg caatttcaag tgttttaaat   2940
gatatccttt cacgtcttga caaagttgag gctgaagtgc aaattgatag gttgatcaca   3000
ggcagacttc aaagtttgca gacatatgtg actcaacaat taattagagc tgcagaaatc   3060
agagcttctg ctaatcttgc tgctactaaa atgtcagagt gtgtacttgg acaatcaaaa   3120
agagttgatt tttgtggaaa gggctatcat cttatgtcct tccctcagtc agcacctcat   3180
ggtgtagtct tcttgcatgt gacttatgtc cctgcacaag aaaagaactt cacaactgct   3240
cctgccattt gtcatgatgg aaaagcacac tttcctcgtg aaggtgtctt tgtttcaaat   3300
ggcacacact ggtttgtaac acaaaggaat ttttatgaac cacaaatcat tactacagac   3360
aacacatttg tgtctggtaa ctgtgatgtt gtaataggaa ttgtcaacaa cacagtttat   3420
gatcctttgc aacctgaatt agactcattc aaggaggagt tagataaata ttttaagaat   3480
catacatcac cagatgttga tttaggtgac atctctggca ttaatgcttc agttgtaaac   3540
attcaaaaag aaattgaccg cctcaatgag gttgccaaga atttaaatga atctctcatc   3600
gatctccaag aacttggaaa gtatgagcag tatataaaat ggccacttaa g            3651
```